US010968472B2

(12) United States Patent
Sherer et al.

(10) Patent No.: US 10,968,472 B2
(45) Date of Patent: Apr. 6, 2021

(54) MULTI-COLOR REPORTER CELLS FOR DETECTING HIV-1

(71) Applicant: Wisconsin Alumni Research Foundation, Madison, WI (US)

(72) Inventors: Nathan Mark Sherer, Madison, WI (US); Jordan Thomas Becker, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 278 days.

(21) Appl. No.: 15/666,082

(22) Filed: Aug. 1, 2017

(65) Prior Publication Data
US 2018/0037925 A1 Feb. 8, 2018

Related U.S. Application Data

(60) Provisional application No. 62/369,908, filed on Aug. 2, 2016.

(51) Int. Cl.
*C12Q 1/04* (2006.01)
*G01N 33/569* (2006.01)
*G01N 33/58* (2006.01)

(52) U.S. Cl.
CPC ......... *C12Q 1/04* (2013.01); *G01N 33/56988* (2013.01); *G01N 33/582* (2013.01); *G01N 2333/16* (2013.01)

(58) Field of Classification Search
None
See application file for complete search history.

(56) References Cited

PUBLICATIONS

Holmes et al., PLoS Pathog, Jun. 18, 2015, 11(6): e1004961. (Year: 2015).*
Bindhu M, Nair A, Lairmore MD (Sep. 2004) "Role of accessory proteins of HTLV-1 in viral replication, T cell activation, and cellular gene expression," *Front Biosci J Virtual Libr.* 1;9:2556-2576.
Campbell, Perez, Melar, and Hope (Apr. 10, 2007) "Labeling HIV-1 virions with two fluorescent proteins allows identification of virions that have productively entered the target cell," *Virology.* 360(2):286-293.
Checkley MA, Luttge BG, Freed EO. (Jul. 2011) "HIV-1 envelope glycoprotein biosynthesis, trafficking, and incorporation," *J Mol Biol.* 410(4):582-608.
Finzi et al (Nov. 14, 1997) "Identification of a reservoir for HIV-1 in patients on highly active antiretroviral therapy," *Science* 278 (5341): 1295-1300.
Finzi et al. (1999): "Latent infection of CD4+ T cells provides a mechanism for lifelong persistence of HIV-1, even in patients on effective combination therapy," *Nat Med.* 5(5):512-7.
Hill M, Tachedjian G, Mak J. (Jan. 2005) "The packaging and maturation of the HIV-1 Pol proteins," *Curr HIV Res.* 3(1):73-85.
Hütter, G; Nowak, D; Mossner, M; et al. (2009) "Long-Term Control of HIV by CCR5 Delta32/Delta32 Stem-Cell Transplantation," *New England Journal of Medicine* 360(7):692-8.
Jin J, Sherer NM, Heidecker G, Derse D, Mothes W. (Jul. 2009) "Assembly of the murine leukemia virus is directed towards sites of cell-cell contact," *PLoS Biol.* 7(7):e1000163.
Lin, Michael Z. .Wang, Lei (Jun. 12, 2008) "Selective Labeling of Proteins with Chemical Probes in Living Cells," *Physiology* 23(3), 131-141.
Lorenzo-Redondo R, Fryer HR, Bedford T, Kim E-Y, Archer J, Kosakovsky Pond SL, et al. (Feb. 2016) "Persistent HIV-1 replication maintains the tissue reservoir during therapy," *Nature.* 4;530(7588):51-6.
Malim MH, Bieniasz PD. (May 2012) "HIV Restriction Factors and Mechanisms of Evasion," *Cold Spring Harb Perspect Med.* 2(5):a006940.
Modesti (2011) "Fluorescent labeling of proteins," *Methods Mol Biol.* 783:101-20.
Mothes W, Sherer NM, Jin J, Zhong P. (Sep. 2010) "Virus cell-to-cell transmission," *J Virol.* 84(17):8360-8368.
Nekhai S, Jeang K-T (Dec. 2006) "Transcriptional and post-transcriptional regulation of HIV-1 gene expression: role of cellular factors for Tat and Rev," *Future Microbiol.* 1(4):417-26.
Palmer S. (2014) "HIV Cure 101: Challenges in identifying and targeting the HIV reservoir." *AIDS 2014* 20th International AIDS Conference.
Petropoulos C. "Retroviral Taxonomy, Protein Structures, Sequences, and Genetic Maps," © 1997, Cold Spring Harbor Laboratory Press (Cold Spring Harbor, New York, USA). Available online at http://www.ncbi.nlm.nih.gov/books/NBK19417 (Book—Copy Not Provided).
Procopio et al. (Jun. 27, 2015) "A Novel Assay to Measure the Magnitude of the Inducible Viral Reservoir in HIV-infected Individuals," *EBioMedicine* 2(8):874-83.
Sauer, Hofkens, and Enderlein, "Handbook of Fluorescence Spectroscopy and Imaging: From Ensemble to Single Molecules 1st Edition," © 2011, Wiley-VCH (Weinheim, Germany), ISBN-13: 978-3527316694 (Book—Copy Not Provided).

* cited by examiner

*Primary Examiner* — Nicole Kinsey White
(74) *Attorney, Agent, or Firm* — Joseph T. Leone, Esq.; Dewitt LLP

(57) ABSTRACT

Disclosed are methods to measure the extent of viral infection and methods to measure latent viral reservoir in cells harboring or suspected of harboring such a reservoir.

18 Claims, 14 Drawing Sheets

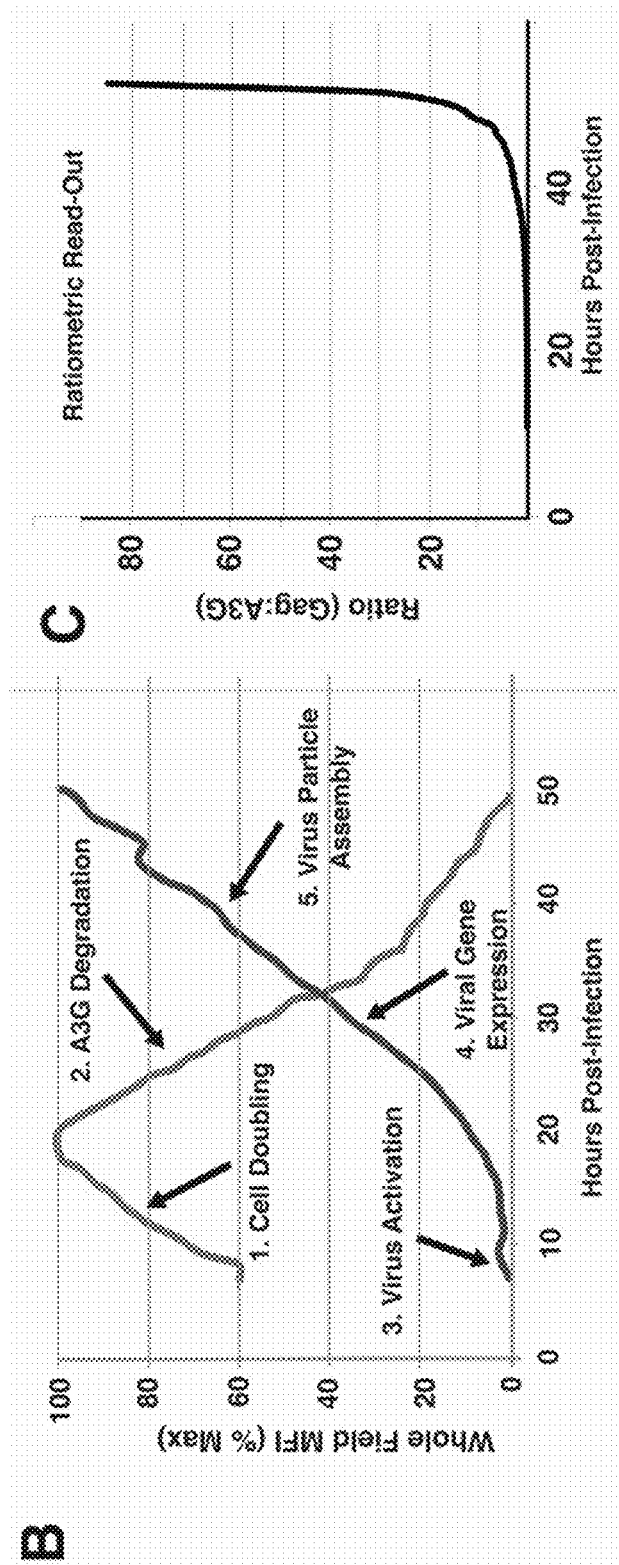

MULTI-COLOR REPORTER CELLS FOR DETECTING HIV-1

CROSS-REFERENCE TO RELATED APPLICATIONS

Priority is hereby claimed to provisional application Ser. No. 62/369,908, filed Aug. 2, 2016, which is incorporated herein by reference.

FEDERAL FUNDING STATEMENT

This invention was made with government support under AI110221 awarded by the National Institutes of Health. The government has certain rights in the invention.

BACKGROUND

The human immunodeficiency type 1 (HIV-1) infects more than 34 million people worldwide and contributes significantly to global morbidity due to HIV/AIDS. HIV-1 establishes a lifelong infection for which there is no cure. Like all viruses, HIV-1 spreads infection among cells, tissues, and people in the form of nanometer-scale particles known as virions. While virions can transmit infection in cell-free form, it has been demonstrated that the spread of retroviral infection is much more efficient when infected cells can form tight, physical cell-to-cell interfaces known as virological synapses (VS's). VS-mediated spread may be the predominant mode of HIV spread in vivo.

A persistent problem in treating HIV invention and perhaps eventually eradicating the virus is that the virus can exist in a latent form, known as the latent HIV reservoir or simply the viral reservoir. In short, HIV-1 is able to persist in a non-virulent, non-pathogenic form by integrating its genome into the host cell DNA. Integration allows the viral genome to remain in the cell as it replicates (from generation to generation). Because there is no production of HIV virions during the latent stage, the dormant state is able to evade host immune responses that require epitopes/antigens to initiate their cascade. The integrated viral genome is replicated along with the cellular genome when the infected cell divides. The integration of the HIV-1 viral genome allows viral reproduction to initiate again later (such as when anti-retroviral chemotherapy is discontinued). The latent HIV reservoir thus consists of infected cells (typically memory T cells) in which HIV is able to persist in the latent phase even when the patient is on anti-retroviral therapy.

The current methods to measure quantitatively the latent HIV reservoir are difficult to perform, time-consuming, and expensive. The two most common assays are the quantitative viral outgrowth assay (QVOA) and Tat/Rev Induced Limiting Dilution Assay (TILDA). These two assays have been described in the scientific literature and will not be described in any detail here. Regarding QVOA, see Finzi et al (14 Nov. 1997) "Identification of a reservoir for HIV-1 in patients on highly active antiretroviral therapy," Science 278(5341):1295-1300. Regarding TILDA, see Procopio et al. (27 Jun. 2015) "A Novel Assay to Measure the Magnitude of the Inducible Viral Reservoir in HIV-infected Individuals," EBioMedicine 2(8):874-83.

These difficult assays are due to a host of factors inherent in the HIV infection process. For one, there are no known extracellular markers that are associated with latently infected cells. Additionally, the reservoir is established in the very early stages of HIV infection, but the exact timing remains unknown. See Palmer S. (2014) "HIV Cure 101: Challenges in identifying and targeting the HIV reservoir." AIDS 2014 20th International AIDS Conference. Latency occurs within infected cells prior to the onset of anti-retroviral chemotherapy; the reservoir once established is not eliminated by anti-retroviral chemotherapy. Chemotherapy does block reactivation of the latent reservoir by blocking the virion reproduction process. However, once chemotherapy is discontinued, the virus can and does reactivate. A means to detect and quantify the reservoir quickly, cheaply, and accurately is critical to evaluating the efficacy of new treatment protocols and putative cures. There is a long-felt and unmet need for a method to detect the presence of replication-competent HIV-1 provirus.

At least one fluorescent assay has been described in the literature for measuring when HIV-1 virions have entered a cell. See Campbell, Perez, Melar, and Hope (10 Apr. 2007) "Labeling HIV-1 virions with two fluorescent proteins allows identification of virions that have productively entered the target cell," Virology. 360(2): 286-293. In this approach, HIV-1 virions were dual-labeled with GFP. Briefly, a fluorescent protein fusion was targeted to the plasma membrane by the addition of the N-terminal 15 amino acid sequence of c-Src (S15). This construct was efficiently packaged into HIV virions. Using fluorescent proteins fused to this sequence, the authors generated virions dually labeled with S15-mCherry and GFP-Vpr. The loss of the S15-mCherry membrane signal can be tracked following fusion. That is, after infection with labeled HIV virions, the authors found a measurable, specific loss of membrane label during infection. This loss of fluorescence was not observed when fusion is prevented using bafilomycin A. The assay thus discriminates between non-productively endocytosed virions and those HIV virions actively undergoing steps in the infectious process.

SUMMARY

Disclosed herein is a method of using multicolor fluorescent reporter cells in a simple, cost-effect, HIV-1 quantitative viral outgrowth assay (Q-VOA). The assay reliably monitors latent virus reservoir size in HIV-1-infected human subjects and non-human primate models of HIV/AIDS. The method uses cells and viruses labeled with at least two, at least three, at least four, at least five, or more than five different fluorescent reporter molecules whose respective fluorescence signals are generated and/or extinguished differentially. By examining the ratios of signals generated by the two or more reporter molecules, the progress of HIV-1 assembly and propagation can be followed via microscopic video. The multicolor fluorescence-based cell readouts respond to HIV-1 infection with high sensitivity and without the need for chemical substrates, thus representing a significant improvement over existing HIV-1 GFP- or chemiluminescent-based single reporter lines. A fundamental benefit of the method derives from coupling at least one first fluorescent marker that turns "on" (i.e., a fluorescent marker that is activated) in response to HIV-1 infection (for example, via a response to HIV-1 Rev or Tat) with at least one second fluorescent marker that is turned "off" (i.e., a fluorescent marker that is deactivated) by an HIV-1 immune modulatory protein (for example Vif, Vpu, or Nef). "Off" markers include fluorescent versions of host proteins APOBEC3G, BST2/Tetherin, and CD4 that are rapidly degraded by HIV-1 Vif, Vpu, and Nef, respectively. Calculating net "on/off" ratios over time for up to five independent fluorescent signals provides for extremely high sensitivity. The method is capable of identifying viral isolates that are prone to latency; that is, viral isolates with reduced Rev or Tat activities. The method is also capable of identifying viral isolates that exhibit suppressor phenotypes (e.g., suboptimal Vif, Vpu, or Nef activities). The HIV-1-responsive reporters may be modified so as to amplify signals more rapidly due to virus-induced cell-cell signaling (paracrine reporters).

The method may be structured in any suitable format, including as a micro-fluidic addressed array.

Without being limited to any underlying mechanism or biological phenomena, the inventors hypothesize that the efficiency of spreading infection reflects the coordination of viral, cellular and extracellular matrix (ECM) factors that regulate the efficiency of virological synapse formation and turnover. The present method thus provides a novel and inventive, quantitative, live-cell imaging platform based on video microscopy and fluorescent retroviruses and/or reporter cells. The method enables direct, real-time monitoring of the biogenesis and transmission of HIV-1 at single cell resolution and over multiple rounds of viral replication. The method is capable of measuring, quantitatively, the latent HIV-1 reservoir in HIV-1-infected humans and in non-human primate models of HIV/AIDS.

Measuring the latent HIV-1 reservoir size is a critical first step in evaluating whether any putative treatment actually reduces the reservoir size. Large reservoirs lead to rapid viral rebound with even brief antiviral therapy interruptions. HIV chemotherapy management is difficult; treatment failure occurs often despite intensive patient monitoring. It is estimated that half of the new HIV infections in the US are from patients who know they are HIV-positive but underestimate their own transmissability. Measuring the latent HIV reservoir in these individuals will reduce the incidence of new HIV infections. Actually reducing the HIV-1 latent reservoir will result in better long-term outcomes for patients, reduce the odds of spreading the infection, and, ideally, provide a baseline for engineering an effective cure strategy.

The latent reservoir size varies several logs between patients. Thus, a method that accurately measures the latent reservoir is key. The reservoir can shrink markedly during drug-based antiretroviral therapy. The latent viral reservoir of one HIV patient (Timothy Ray Brown, known as The "Berlin Patient") has been successfully eradicated. See Hütter, G; Nowak, D; Mossner, M; et al. (2009) "Long-Term Control of HIV by CCR5 Delta32/Delta32 Stem-Cell Transplantation," *New England Journal of Medicine* 360(7):692-8. In short, advances in reservoir monitoring are needed so that patient-specific measurements can guide decision-making.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present method shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods disclosed herein can comprise, consist of, or consist essentially of the elements and limitations of the method described herein, as well as any additional or optional ingredients, components, or limitations described herein or otherwise useful in biochemistry and the imaging of live cells using confocal microscopy and fluorescent reporter molecules.

BRIEF DESCRIPTION OF THE DRAWINGS

FIG. 2E is 12 hours. Images generated from VSVg pseudotyped HIV-1 cyan fluorescent protein (CFP) expressed from Nef position.

As shown in FIG. 3B, using the ratio of activation:degradation fluorescence provides ~10-fold increase to sensitivity of the assay.

FIG. 7B is a graph depicting whole-field mean fluorescence intensity (MFI) as a function of time (hours post-infection). Useful features of the cells are that they provide dynamic, whole-field measures of YFP-A3G and Gag-mChe fluorescence signatures allowing for direct measurements of: (1) cell doubling rate; (2) A3G downregulation kinetics; (3) viral gene activation; (4) rates of viral late gene expression; and (5) onset of virus particle production (based on changes to cell granularity).

FIG. 7C is a graph depicting the ratio Gag:A3G. This graph illustrates another useful feature of the cells is that signal-to-noise can be reduced through ratioing the relative measurements of YFP-A3G and Gag-mCherry signals.

DETAILED DESCRIPTION

Figure 1:
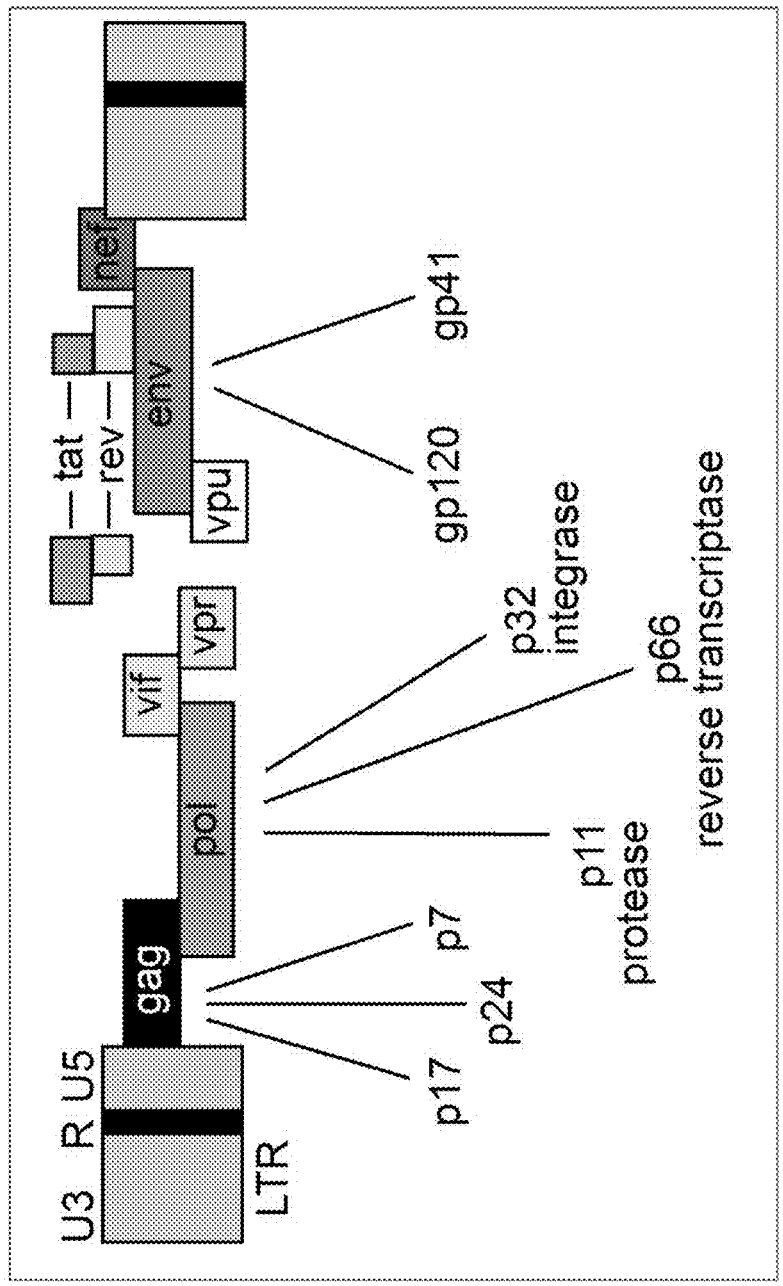
FIG. 1 is a schematic diagram of the genome of HIV-1.

Disclosed herein are reporter cell lines having two or more differentially detectable fluorescent labels or reporter molecules for detecting and studying patient-derived viruses. These highly sensitive and specific reporter cell lines are suitable for automated detection of HIV in a microfluidic chamber. Accordingly, disclosed herein are 2-, 3-, 4, 5- and more than 5-color fluorescence based cell read-outs that respond robustly to HIV-1 infection. The cells and the method that uses them are thus useful both for tracking the spread of HIV-1 infection but are also ideal for implementation into an automated Q-VOA assay.

The reporter cells are based on coupling fluorescent markers that are turned "on" in response to HIV infection by viral trans-acting factors (e.g., Rev and Tat) to markers turned "off" by the virus (e.g., YFP-tagged versions of the antiviral proteins APOBEC3G or BST2/Tetherin that are rapidly degraded by the viral proteins Vif or Vpu). Calculating net "on/off" ratios over time, relative to standards, allows for high sensitivity and favorable signal-to-noise. The ability to amplify response signals with minimal background and without the need for chemical substrates thus represents a significant improvement over existing HIV-1 GFP- or chemiluminescent-based single reporter lines.

Thus, a first version of the method is a method of tracking viral infection in a cell. The method comprises providing a cell susceptible to infection by a virus in which the cell contains at least two differentially labeled proteins: a first protein labeled with a first fluorophore whose signal is up-regulated upon infection of the cell by the virus and a second protein labeled with a second fluorophore that is down-regulated upon infection of the cell by the virus. The cell is exposed to the virus under conditions where the virus can infect the cells. Fluorescent signals generated by the first fluorophore and the second fluorophore are measured. The extent of infection of the cell by the virus is determined by comparing the fluorescent signals measured in the test cells with corresponding signals generated in a corresponding control cell not exposed to the virus. Significant changes in the signals generated by the fluorophores indicates infection of the cells by the virus.

The virus may be an HIV virus, such as HIV-1 virus or a related non-human primate virus, such as variants of simian immunodeficiency virus (SIV). The cell may be a human T-cell or a non-human primate cell. For example, the cell may be a HeLa cell or a Jurkat cell.

The first protein may be a reporter responsive to HIV Tat (trans-activator of transcription) or HIV Rev. The second protein may be any or all of A3G (apolipoprotein B mRNA editing enzyme), BST2 (bone marrow stromal antigen 2, also known as tetherin), CD4 (cluster of differentiation 4), and SERINC5 (serine incorporator 5).

Optionally, the cell may contain a third protein labeled with a third fluorophore and wherein the third fluorophore generates a fluorescent signal that is distinct from and can be detected independently of the signals generated by the first and second fluorophores, and wherein fluorescent signals generated from the third fluorophore are detectably altered upon infection of the cell with the virus.

Optionally, the cell may contain a fourth protein labeled with a fourth fluorophore and wherein the fourth fluorophore generates a fluorescent signal that is distinct from and can be detected independently of the signals generated by the first, second, and third fluorophores, and wherein fluorescent signals generated from the fourth fluorophore are detectably altered upon infection of the cell with the virus.

Optionally, the cell may contain a fifth protein labeled with a fifth fluorophore and wherein the fifth fluorophore generates a fluorescent signal that is distinct from and can be detected independently of the signals generated by the first, second, third, and fourth fluorophores, and wherein fluorescent signals generated from the fifth fluorophore are detectably altered upon infection of the cell with the virus.

Another version of the method is a method of quantitating a latent viral reservoir of a cell suspected of being infected with a latent virus. Here, the method comprises providing a cell suspected of harboring a latent viral reservoir in which the cell contains at least two differentially labeled proteins: a first protein labeled with a first fluorophore whose signal is up-regulated upon activation of virus in the latent viral reservoir and a second protein labeled with a second fluorophore that is down-regulated upon activation of virus in the latent viral reservoir. The cell is exposed to an agent capable of inducing activation of the latent virus. Fluorescent signals generated by the first fluorophore and the second fluorophore are measured. The latent viral reservoir in the cell is quantitated by comparing the fluorescent signals measured in step (c) with corresponding signals generated in a corresponding cell known not to contain a latent viral reservoir and exposed to the same agent capable of inducing activation of the latent virus.

The latent viral reservoir may comprise a latent HIV virus, such as latent HIV-1 virus.

The cell may be a human T-cell. The cell may be a non-human primate cell.

The first protein may be a reporter responsive to Tat (trans-activator of transcription) or a reporter responsive to Rev. The second protein may be A3G, BST2, CD4, and SERINC5.

Optionally, the cell contains a third protein labeled with a third fluorophore and wherein the third fluorophore generates a fluorescent signal that is distinct from and can be detected independently of the signals generated by the first and second fluorophores, and wherein fluorescent signals generated from the third fluorophore are detectably altered upon activation of the latent viral reservoir.

Optionally, the cell contains a fourth protein labeled with a fourth fluorophore and wherein the fourth fluorophore generates a fluorescent signal that is distinct from and can be detected independently of the signals generated by the first, second, and third fluorophores, and wherein fluorescent signals generated from the fourth fluorophore are detectably altered activation of the latent viral reservoir.

Optionally, the cell contains a fifth protein labeled with a fifth fluorophore and wherein the fifth fluorophore generates a fluorescent signal that is distinct from and can be detected independently of the signals generated by the first, second, third, and fourth fluorophores, and wherein fluorescent signals generated from the fifth fluorophore are detectably altered upon activation of the latent viral reservoir.

Delving specifically into the machinations of retroviruses, in addition to AIDS, the retroviruses human immunodeficiency virus type 1 (HIV-1) and human T lymphotropic virus type 1 (HTLV-1) also cause human cancers. These retroviruses exploit cell-cell contacts to enhance the spread of persistence of infection in lymphocytes See, for example, Mothes W, Sherer N M, Jin J, Zhong P. (September 2010) "Virus cell-to-cell transmission," *J Virol.* 84(17):8360-8368. All retroviruses encode three polyproteins required for infectious virion production: Group specific antigen (Gag), Polymerase (Pol) and Envelope (Env). See Petropoulos C. "Retroviral Taxonomy, Protein Structures, Sequences, and Genetic Maps," © 1997, Cold Spring Harbor Laboratory Press (Cold Spring Harbor, N.Y., USA). Available online at http://www.ncbi.nlm.nih.gov/books/NBK19417. HIV-1 and other complex retroviruses such HTLV-1 also encode additional proteins that regulate viral gene expression and antagonize the host immune response. See Malim M H, Bieniasz P D. (May 2012) "HIV Restriction Factors and Mechanisms of Evasion," *Cold Spring Harb Perspect Med.* 2(5):a006940; Nekhai S, Jeang K-T (December 2006) "Transcriptional and post-transcriptional regulation of HIV-1 gene expression: role of cellular factors for Tat and Rev," *Future Microbiol.* 1(4):417-26; and Bindhu M, Nair A, Lairmore M D (September 2004) "Role of accessory proteins of HTLV-1 in viral replication, T cell activation, and cellular gene expression," *Front Biosci J Virtual Libr.* 1; 9:2556-2576.

Specifically relevant to the present method is that HIV-1 encodes two gene regulatory factors, Rev and Tat, and four immunomodulatory factors: Vif, Vpr, Vpu, and Nef. See FIG. 1, which is a schematic diagram of the HIV-1 genome. Gag is the viral assembly machine that, for "C-type" retroviruses such as HIV-1, HTLV-1 and the simple onco-retrovirus murine leukemia virus (MLV), drives virus particle biogenesis at the plasma membrane. In this process, Gag encapsidates two copies of the viral genomic RNA (gRNA) and acquires a protective, cell-derived lipid envelope bilayer. Ono A. (2009) "HIV-1 Assembly at the Plasma Membrane: Gag Trafficking and Localization," *Future Virol.* 4(3):241-57. Although Gag expression is sufficient to generate virus-like particles in the absence of other viral factors, Pol, Env, and two copies of gRNA must be incorporated into virions in order for them to be infectious. Pol is delivered to virion assembly sites in the form of Gag-Pol fusion proteins that, during virion maturation, are cleaved to generate the viral enzymes Protease, Reverse Transcriptase and Integrase. See Hill M, Tachedjian G, Mak J. (January 2005) "The packaging and maturation of the HIV-1 Pol proteins," *Curr HIV Res.* 3(1):73-85. Envelope (Env) glycoproteins are type I transmembrane proteins that mediate viral entry. Env is cleaved in the endoplasmic reticulum to generate transmembrane (TM) and surface (SU) subunits prior to delivery to assembly sites through the secretory pathway in the form of SU-TM trimers. Checkley M A, Luttge B G, Freed E Q. (July 2011) "HIV-1 envelope glycoprotein biosynthesis, trafficking, and incorporation," *J Mol Biol.* 410(4):582-608.

This provides an opportunity to tag two or more of the proteins involved with HIV-1 infection and propagation to be tagged, and thereby to follow the fate of the viral genomic RNA. The method is capable of directly monitoring how gRNAs, Gag, and Env are coordinately trafficked to the plasma membrane. After virion assembly, budding, and release, Env trimers must bind to both CD4 receptors and a chemokine co-receptor (CCR5 or CXCR4) found on the surface of susceptible T cells and macrophages. Coreceptor binding triggers conformational changes in Env resulting in virion-cell membrane fusion and delivery of viral capsids to the target cell cytoplasm prior to reverse transcription of a viral cDNA and integration of the DNA provirus into the host cellular chromatin. For many retroviruses, proviral integration leads to gene dysregulation associated with the evolution of cancer. HIV-1's integration into resting memory T cells serves as the basis for establishing the long-term latent viral reservoir that leads to AIDS. See Finzi D, Blankson J, Siliciano J D, Margolick J B, Chadwick K, Pierson T, et al. (1999): "Latent infection of CD4+ T cells provides a mechanism for lifelong persistence of HIV-1, even in patients on effective combination therapy," *Nat Med.* 5(5):512-7.

Most retroviruses are able to spread infection via cell-free virions, wherein infectious virions are released from cells to diffuse through the extracellular milieu prior to binding to uninfected target cells bearing appropriate entry receptors. However, spread of infection can be up to 10,000-fold more efficient when infected cells can form physical contacts with uninfected cells referred to as "virological synapses" (VS's). For HIV-1, VS formation is driven, in part, through interactions between viral Env glycoproteins on the infected cell surface and CD4 receptors on the uninfected cell. VS-mediated spread is likely advantageous to HIV-1 and other retroviruses for several reasons. First, contacts directly couple the processes of viral egress and entry in space and time, thereby providing a kinetic advantage. Second, large numbers of virions are transferred simultaneously from cell to cell at the VS (i.e., there is high multiplicity infection), providing a mechanism by which the virus may be able to overwhelm select antiviral factors. Third, some retroviruses have adapted more sophisticated, signal-based mechanisms of exploiting cell-cell contacts to enhance the spread of infection. For example, it has been shown that MLV Env glycoproteins, in addition to their role as fusion machines, function as cell surface adhesion factors that signal virion assembly to occur preferentially at the site of cell-cell contact. See Jin J, Sherer N M, Heidecker G, Derse D, Mothes W. (July 2009) "Assembly of the murine leukemia virus is directed towards sites of cell-cell contact," *PLoS Biol.* 7(7):e1000163. In preliminary data (not shown), the present inventors have demonstrated that the same is likely true for HIV-1 Env, although the mechanism is not yet understood.

Without being limited to any underlying mechanism, the present inventors hypothesize that Env has, for multiple viruses, evolved to serve as a critical "sensor" for detecting neighboring receptor-expressing cells, thus ensuring a rapid, directional flow of infectious material.

It is likely that HIV-1 exploits several different modes of transmission during acute infection in order to efficiently access susceptible CD4+ T cells in targeted lymphoid tissues including the gut-associated lymphoid tissue (GALT), spleen, and lymph nodes. These modes include cell-free transmission, VS-mediated transfer from infected and uninfected T cells, and trans-infection, a mode of spread wherein virions associate with the plasma membrane of migratory, uninfected cells (typically dendritic cells) that subsequently deliver infectious virions to unsuspecting target cells during instances of transient cell-cell contact.

Ex vivo, the VS can protect HIV-1 transmission from neutralizing antibodies, antiviral drugs, or host restriction factors. However, the in vivo relevance of the VS to HIV-1 spread and persistence is still unclear. That said, there is growing evidence that ongoing replication continues in dense lymphoid tissues of infected individuals despite long-term therapy. Lorenzo-Redondo R, Fryer H R, Bedford T, Kim E-Y, Archer J, Kosakovsky Pond S L, et al. (February 2016) "Persistent HIV-1 replication maintains the tissue reservoir during therapy," *Nature.* 4; 530(7588):51-6. Moreover, multiple groups have shown that VS-mediated spread and trans-infection can occur in vivo using intravital imaging in infected mouse models.

Thus, disclosed herein is a quantitative virus outgrowth assay (Q-VOA) capable of detecting and measuring viral reservoirs in infected people. To test and optimize the cell lines for such an assay, de-identified CD4+ T cells isolated from long-term HIV-1 infected individuals who are on or off antiretroviral therapy, as well as from HIV-negative donors are obtained. These cells are then incubated with YFP-A3G/HIVmCherry reporter HeLa and/or Jurkat cells (see FIG. 5) in 24-well glass bottomed dishes. Because a subset of cells may be latently infected (and quantitatively measuring the extent of the latent infection is the goal of the method), a subset of these cells will be treated with histone deacetylase (HDAC) inhibitors to activate latent virus prior to washing and adding reporter cells. Cultures will be monitored using an automated microscope with whole well images acquired every 24 hours to measure changes to mCherry/YFP expression ratios over time. The sensitivity of the assay is determined in co-cultures using spiked HIV-1 infected cells at quantities from one donor cell per 100,000 target cells to one donor per 20 million T cells. A cell line model for latency (e.g., ACH-2 that carries a single integrated provirus and is inducible with PMA to produce infectious HIV-1) will be used as a positive control. This reagent is available from the NIH AIDS Reagent Program.

The method described herein uses differential labeling with at least two different fluorophores to generate distinct signals in response to HIV-1 infection of a cell. The signals may be diametrically opposed (i.e., one is deactivated as the other is activated), but this is not required. The signals, however, must be distinguishable from one another, either by whether they are activated or deactivated in response to HIV-1 infection of the test cells or via the wavelengths at which they absorb and emit photons. It is preferred that the excitation and emission wavelengths are in the visible region, although this is not strictly required. Fluorophores that absorb or emit at wavelengths above and below the visible spectrum may be used. A very large number of suitable fluorophores are known and commercially available. The term "fluorophore" is used broadly herein to encompass any and all of them. An exemplary, non-limiting list fluorophores that may be used in the present method are contained in Table 1:

TABLE 1

Fluorophores that may be used in the present method:

| Fluorophore | Absorption | Emission | Other info |
|---|---|---|---|
| 1,5 IAEDANS | 336 | 490 | |
| 1,8-ANS | 372 | 480 | |
| 4-Methylumbelliferone | 385 | 502 | |
| 5-carboxy-2,7-dichlorofluorescein | 504 | 529 | |
| 5-Carboxyfluorescein (5-FAM) | 492 | 518 | |
| 5-Carboxynapthofluorescein (pH 10) | 512/598 | 563/668 | Ratio Dye, pH |
| 5-Carboxytetramethylrhodamine (5-TAMRA) | 542 | 568 | |
| 5-FAM (5-Carboxyfluorescein) | 492 | 518 | |
| 5-HAT (Hydroxy Tryptamine) | 370-415 | 520-540 | |
| 5-Hydroxy Tryptamine (HAT) | 370-415 | 520-540 | |
| 5-ROX (carboxy-X-rhodamine) | 578 | 604 | |
|  | 567 | 591 | |
| 5-TAMRA (5-Carboxytetramethylrhodamine) | 548 | 552 | |
|  | 542 | 568 | |
| 6-Carboxyrhodamine 6G | 518 | 543 | |
| 6-CR 6G | 518 | 543 | |
| 6-JOE | 520 | 548 | |
| 7-Amino-4-methylcoumarin | 351 | 430 | |
| 7-Aminoactinomycin D (7-AAD) | 546 | 647 | |
| 7-Hydroxy-4-methylcoumarin | 360 | 449, 455 | |
| 9-Amino-6-chloro-2-methoxyacridine | 412, 430 | 471, 474 | |
| ABQ | 344 | 445 | |
| Acid Fuchsin | 540 | 630 | |
| ACMA (9-Amino-6-chloro-2-methoxyacridine) | 412, 430 | 471, 474 | |
| Acridine Orange + DNA | 502 | 526 | |
| Acridine Orange + RNA | 460 | 650 | |
| Acridine Orange, both DNA & RNA | 440-480 | 520-650 | |
| Acridine Red | 455-600 | 560-680 | |
| Acridine Yellow | 470 | 550 | |
| Acriflavin | 436 | 520 | |
| Acriflavin Feulgen SITSA | 355-425 | 460 | |
| Aequorin (Photoprotein) | | 466 | Photoprotein |
| AFPs-AutoFluorescent Protein-(Quantum Biotechnologies) see sgGFP, sgBFP | | | |
| Alexa Fluor 350 ™ | 346 | 442 | |
|  | 342 | 441 | |

TABLE 1-continued

Fluorophores that may be used in the present method:

| Fluorophore | Absorption | Emission | Other info |
| --- | --- | --- | --- |
| Alexa Fluor 430 ™ | 431 | 540 | |
| Alexa Fluor 488 ™ | 495, 492 | 519, 520 | |
| Alexa Fluor 532 ™ | 531, 532 | 553, 554 | |
| Alexa Fluor 546 ™ | 556, 557 | 572, 573 | |
| Alexa Fluor 568 ™ | 577, 578 | 603 | |
| Alexa Fluor 594 ™ | 590, 594 | 617, 618 | |
| Alexa Fluor 633 ™ | 632 | 650 | |
| Alexa Fluor 647 ™ | 647 | 666 | |
| Alexa Fluor 660 ™ | 668 | 698 | |
| Alexa Fluor 680 ™ | 679 | 702 | |
| Alizarin Complexon | 530-560, 580 | 580, 624-645 | |
| Alizarin Red | 530-560 | 580 | |
| Allophycocyanin (APC) | 630, 645 | 655, 660 | |
| AMC, AMCA-S | 345 | 445 | |
| AMCA (Aminomethylcoumarin) | 345 | 425 | |
| | 347 | 444 | |
| AMCA-X | 353 | 442 | |
| Aminoactinomycin D | 555 | 655 | |
| Aminocoumarin | 346 | 442 | |
| | 350 | 445 | |
| Aminomethylcoumarin (AMCA) | 345 | 425 | |
| | 347 | 444 | |
| Anilin Blue | | 600 | |
| Anthrocyl stearate | 360-381 | 446 | |
| APC (Allophycocyanin) | 630, 645 | 655, 660 | |
| APC-Cy7 | 625-650 | 755 | |
| APTRA-BTC = Ratio Dye, Zn2+ | 466/380 | 520/530 | Ratio Dye, Zn2+ |
| APTS | 424 | 505 | |
| Astrazon Brilliant Red 4G | 500 | 585 | |
| Astrazon Orange R | 470 | 540 | |
| Astrazon Red 6B | 520 | 595 | |
| Astrazon Yellow 7 GLL | 450 | 480 | |
| Atabrine | 436 | 490 | |
| ATTO-TAG ™ CBQCA | 465 | 560 | |
| ATTO-TAG ™ FQ | 486 | 591 | |
| Auramine | 460 | 550 | |
| Aurophosphine G | 450 | 580 | |
| Aurophosphine | 450-490 | 515 | |
| BAO 9 (Bisaminophenyloxadiazole) | 365 | 395 | |
| BCECF (high pH) | 492, 503 | 520, 528 | |
| BCECF (low pH) | 482 | 520 | |
| Berberine Sulphate | 430 | 550 | |
| Beta Lactamase | 409 | 447, 520 | |
| BFP blue shifted GFP (Y66H) Blue Fluorescent Protein | 381, 382, 383 | 445, 447, 448 | blue shifted GFP (Y66H) Blue Fluorescent Protein |
| BFP/GFP FRET | | | |
| Bimane | 398 | 490 | |
| Bisbenzamide | 360 | 461 | |
| Bisbenzimide (Hoechst) | 360 | 461 | |
| bis-BTC = Ratio Dye, Zn2+ | 455/405 | 529/505 | Ratio Dye, Zn2+ |
| Blancophor FFG | 390 | 470 | |
| Blancophor SV | 370 | 435 | |
| BOBO ™-1 | 462 | 481 | |
| BOBO ™-3 | 570 | 602 | |
| Bodipy 492/515 | 490 | 515 | |
| Bodipy 493/503 | 533 | 549 | |
| Bodipy 500/510 | 509 | 515 | |
| Bodipy 505/515 | 502 | 510 | |
| Bodipy 530/550 | 528 | 547 | |
| Bodipy 542/563 | 543 | 563 | |
| Bodipy 558/568 | 558 | 569 | |
| Bodipy 564/570 | 564 | 570 | |
| Bodipy 576/589 | 579 | 590 | |
| Bodipy 581/591 | 584 | 592 | |
| Bodipy 630/650-X | 625 | 642 | |
| Bodipy 650/665-X | 647 | 665 | |
| Bodipy 665/676 | 605 | 676 | |
| Bodipy Fl | 504, 505 | 511, 513 | |
| Bodipy FL ATP | 505 | 514 | |
| Bodipy Fl-Ceramide | 505 | 511 | |
| Bodipy R6G SE | 528 | 547 | |
| Bodipy TMR | 542 | 574 | |
| Bodipy TMR-X conjugate | 544 | 573 | |
| Bodipy TMR-X, SE | 544 | 570 | |

TABLE 1-continued

Fluorophores that may be used in the present method:

| Fluorophore | Absorption | Emission | Other info |
| --- | --- | --- | --- |
| Bodipy TR | 589 | 617 | |
| Bodipy TR ATP | 591 | 620 | |
| Bodipy TR-X SE | 588 | 616 | |
| BO-PRO™-1 | 462 | 481 | |
| BO-PRO™-3 | 544 | 570 | |
| Brilliant Sulphoflavin FF | 430 | 520 | |
| BTC-Ratio Dye Ca2+ | 464/401 | 533/529 | Ratio Dye Ca2+ |
| BTC-5N-atio Dye, Zn2+ | 459/417 | 517/532 | Ratio Dye, Zn2+ |
| Calcein | 494 | 517 | |
| Calcein Blue | 373 | 440 | |
| Calcium Crimson ™ | 588, 589 | 611, 615 | |
| Calcium Green | 501, 506 | 531 | |
| Calcium Green-1 Ca2+ Dye | 506 | 531 | Ca2+ Dye |
| Calcium Green-2 Ca2+ | 506/503 | 536 | Ca2+ |
| Calcium Green-5N Ca2+ | 506 | 532 | Ca2+ |
| Calcium Green-C18 Ca2+ | 509 | 530 | Ca2+ |
| Calcium Orange | 549 | 575 576 | |
| Calcofluor White | 385, 395, 405 | 437, 440, 445 | |
| Carboxy-X-rhodamine (5-ROX) | 576 | 601 | |
| Cascade Blue ™ | 377 398 399 | 420 423 | |
| Cascade Yellow | 399 400 | 550 552 | |
| Catecholamine | 410 | 470 | |
| CCF2 (GeneBlazer) | | | |
| CFDA | 494 | 520 | |
| CFP-Cyan Fluorescent Protein | 430, 433, 436, (453) | 474, 475, 476, (501) | Cyan Fluorescent Protein |
| CFP/YFP FRET | | | |
| Chlorophyll | 480 | 650 | |
| Chromomycin A | 436-460 | 470 | |
| Chromomycin A | 445 | 575 | |
| CL-NERF (Ratio Dye, pH) | 504/514 | 540 | Ratio Dye, pH |
| CMFDA | 494 | 520 | |
| Coelenterazine Ca2+ Dye, bioluminescence | (429) | 465 | Ca2+ Dye, bioluminescence, native molecule |
| Coelenterazine cp (Ca2+ Dye,) | (430) | 442 | Ca2+ Dye, bioluminescence |
| Coelenterazine f | (437) | 473 | Ca2+ Dye, bioluminescence |
| Coelenterazine fcp | | 452 | Ca2+ Dye, bioluminescence |
| Coelenterazine h | (437) | 464 | Ca2+ Dye, bioluminescence |
| Coelenterazine hcp | (433) | 444 | Ca2+ Dye, bioluminescence |
| Coelenterazine ip | | 441 | Ca2+ Dye, bioluminescence |
| Coelenterazine n | (431) | 467 | Ca2+ Dye, bioluminescence |
| Coelenterazine O | 460 | 575 | |
| Coumarin Phalloidin | 387 | 470 | |
| C-phycocyanine | | | |
| CPM Methylcoumarin | 384 | 469 | Methylcoumarin |
| CTC | 400-450 | 602 | |
| CTC Formazan | | | |
| Cy2 ™ | 489 | 506 | |
| Cy3.1 8 | 554 | 568 | |
| Cy3.5 ™ | 581 | 598 | |
| Cy3 ™ | 514 552 554 | 566 570 | |
| Cy5.1 8 | 649 | 666 | |
| Cy5.5 ™ | 675 | 695 | |
| Cy5 ™ | 649 | 666 670 | |
| Cy7 ™ | 710, 743 | 767, 805 | |
| Cyan GFP | 433 (453) | 475 (501) | |
| cyclic AMP Fluorosensor (FiCRhR) | 500 | 517 | |
| CyQuant Cell Proliferation Assay | 480 | 520 | Cell Proliferation Assay |

TABLE 1-continued

Fluorophores that may be used in the present method:

| Fluorophore | Absorption | Emission | Other info |
|---|---|---|---|
| Dabcyl | 453 | | |
| Dansyl | 340 | 578 | |
| Dansyl Amine | 337 | 517 | |
| Dansyl Cadaverine | 335 | 518 | |
| Dansyl Chloride | 372 | 518 | |
| Dansyl DHPE | 336 | 517 | |
| Dansyl fluoride | 356 | none | |
| DAPI | 359 | 461 | |
| Dapoxyl | 403 | 580 | |
| Dapoxyl 2 | 374 | 574 | |
| Dapoxyl 3 | 373 | 574 | |
| DCFDA | 504 | 529 | |
| DCFH (Dichlorodihydrofluorescein Diacetate) | 505 | 535 | |
| DDAO | 463 | 607 | |
| DHR (Dihydorhodamine 123) | 505 | 534 | |
| Di-4-ANEPPS | 496 | 705 | |
| Di-8-ANEPPS (non-ratio) | 488 | 605 | |
| | 498 | 713 | |
| DiA (4-Di-16-ASP) | 456 | 591 | |
| Dichlorodihydrofluorescein Diacetate (DCFH) | 505 | 535 | |
| DiD-Lipophilic Tracer | 644 | 665 | Lipophilic Tracer |
| DiD (DiIC18(5)) | 644 | 665 | |
| DIDS | 341 | 415 | |
| Dihydorhodamine 123 (DHR) | 505 | 535 | |
| DiI (DiIC18(3)) | 549, 551 | 565 | |
| Dinitrophenol | 349 | | |
| DiO (DiOC18(3)) | 484, 487 | 501, 502 | |
| DiR | 748 | 780 | Lipophilic Tracer |
| DiR (DiIC18(7)) | 750 | 779 | |
| DM-NERF (high pH) | 497/510 | 540 | Ratio Dye, pH |
| DNP | 349 | | |
| Dopamine | 340 | 490-520 | |
| DsRed | 558 | 583 | Red fluorescent protein |
| DTAF | 494 | 520 | |
| DY-630-NHS | 621 | 660 | Hemicyane label for proteins and DNA |
| DY-635-NHS | 634 | 664 | Hemicyane label for proteins and DNA |
| EBFP | 383 | 447 | Enhanced Blue Fluorescent Protein |
| ECFP | 436 | 474 | Enhanced Cyan Fluorescent Protein |
| EGFP | 488, 498 | 507, 516 | Enhanced Green Fluorescent Protein |
| ELF 97 | 345 | 530 | |
| Eosin | 524 | 545 | |
| Erythrosin | 529, 532 | 554, 555 | |
| Erythrosin ITC | 529 | 555 | |
| Ethidium Bromide | 510, 523 | 595, 605 | |
| Ethidium homodimer-1 (EthD-1) | 528 | 617 | |
| Euchrysin | 430 | 540 | |
| EukoLight | | | |
| Europium (III) chloride | | | |
| EYFP | 513, 520 | 527, 532 | Enhanced Yellow Fluorescent Protein |
| Fast Blue | 360 | 440 | |
| FDA | 494 | 520 | |
| Feulgen (Pararosaniline) | 570 | 625 | |
| FT (Formaldehyd Induced Fluorescence) | 405 | 433 | |
| FITC | 490, 494 | 520, 525 | |
| FITC Antibody | 493 | 517 | |
| Flazo Orange | 375-530 | 612 | |
| Fluo-3 | 480-506, 506 | 520, 527 | |

TABLE 1-continued

Fluorophores that may be used in the present method:

| Fluorophore | Absorption | Emission | Other info |
|---|---|---|---|
| Fluo-4 | 494 | 516 | |
| Fluorescein (FITC) | 490, 494 | 520, 525 | |
| Fluorescein Diacetate | 494 | 520 | |
| Fluoro-Emerald | 495 | 524 | |
| Fluoro-Gold (Hydroxystilbamidine) | 361 | 536 | |
| Fluor-Ruby | 555 | 582 | |
| FluorX | 494 | 520 | |
| FM 1-43 ™ | 479 | 598 | |
| FM 4-46 | 515 | 640 | |
| Fura Red ™ (high pH) | 572 | 657 | |
| Fura Red ™/Fluo-3 | | | |
| Fura-2, high calcium | 335 | 505 | Excitation ratio dye |
| Fura-2, low calcium | 363 | 512 | Excitation ratio dye |
| Fura-2/BCECF | | | |
| Genacryl Brilliant Red B | 520 | 590 | |
| Genacryl Brilliant Yellow 10GF | 430 | 485 | |
| Genacryl Pink 3G | 470 | 583 | |
| Genacryl Yellow 5GF | 430 | 475 | |
| GeneBlazer (CCF2) | | | |
| GFP (S65T) | 498 | 516 | |
| GFP red shifted (rsGFP) | 498 | 516 | |
| GFP wild type, non-UV excitation (wtGFP) | 475 | 509 | |
| GFP wild type, UV excitation (wtGFP) | 395 | 509 | |
| GFPuv | 385 | 508 | |
| Gloxalic Acid | 405 | 460 | |
| Granular Blue | 355 | 425 | |
| Haematoporphyrin | 530-560 | 580 | |
| Hoechst 33258 | 345 | 487 | |
| Hoechst 33342 | 347 | 483 | |
| Hoechst 34580 | 392 | 440 | |
| HPTS | 355 | 465 | |
| Hydroxycoumarin | 325-360 | 386-455 | |
| Hydroxystilbamidine (FluoroGold) | 361 | 536 | |
| Hydroxytryptamine | 400 | 530 | |
| Indo-1, high calcium | 330 | 401 | Emission ratio dye |
| Indo-1, low calcium | 346 | 475 | Emission ratio dye |
| Indodicarbocyanine (DiD) | 644 | 665 | |
| Indotricarbocyanine (DiR) | 748 | 780 | |
| Intrawhite Cf | 360 | 430 | |
| JC-1 | 514 | 529 | |
| JO-JO-1 | 530 | 545 | |
| JO-PRO-1 | 532 | 544 | |
| LaserPro | 795 | 812 | |
| Laurodan | 355 | 460 | |
| LDS 751 (DNA) | 543 | 712 | |
| LDS 751 (RNA) | 590 | 607 | |
| Leucophor PAF | 370 | 430 | |
| Leucophor SF | 380 | 465 | |
| Leucophor WS | 395 | 465 | |
| Lissamine Rhodamine | 572, 577 | 591, 592 | |
| Lissamine Rhodamine B | 577 | 592 | |
| LIVE/DEAD Kit Animal Cells Calcein/Ethidium homodimer | 494 528 | 517 617 | for more details refer to www.probes.com |
| LOLO-1 | 566 | 580 | |
| LO-PRO-1 | 568 | 581 | |
| Lucifer Yellow | 425, 428 | 528, 536, 540 | |
| Lyso Tracker Blue | 373 | 422 | |
| Lyso Tracker Blue-White | 466 | 536 | |
| Lyso Tracker Green | 504, 534 | 511, 551 | |
| Lyso Tracker Red | 490 | 516 | |
| Lyso Tracker Yellow | 551 | 576 | |
| LysoSensor Blue | 374 | 424 | |
| LysoSensor Green | 442 | 505 | |
| LysoSensor Yellow/Blue | 384 | 540 | |
| Mag Green | 507 | 531 | |
| Magdala Red (Phloxin B) | 524 | 600 | |
| Mag-Fura Red | 483/427 | 659/631 | Ratio Dye, $Mg^{2+}$ |

TABLE 1-continued

Fluorophores that may be used in the present method:

| Fluorophore | Absorption | Emission | Other info |
|---|---|---|---|
| Mag-Fura-2 | 369/329 | 508 | Ratio Dye Ca2+ |
|  | 369/330 | 511/491 | Ratio Dye Mg2+ |
| Mag-Fura-5 | 369/330 | 505/500 | Ratio Dye, Ca2+ |
|  | 369/332 | 505/482 | Ratio Dye, Mg2+ |
| Mag-Indo-1 | 349/328 | 480/390 | Ratio Dye, Ca2+ |
|  | 349/330 | 480/417 | Ratio Dye, Mg2+ |
| Magnesium Green | 506, 507 | 531 |  |
| Magnesium Orange | 550 | 575 |  |
| Malachite Green | 628 |  |  |
| Marina Blue | 362 | 459 |  |
| Maxilon Brilliant Flavin 10 GFF | 450 | 495 |  |
| Maxilon Brilliant Flavin 8 GFF | 460 | 495 |  |
| Merocyanin | 555 | 578 |  |
| Methoxycoumarin | 360 | 410 |  |
| Mitotracker Green FM | 490 | 516 |  |
| Mitotracker Orange | 551 | 576 |  |
| Mitotracker Red | 578 | 599 |  |
| Mitramycin | 450 | 470 |  |
| Monobromobimane | 398 | 490 |  |
| Monobromobimane (mBBr-GSH) | 398 | 500 |  |
| Monochlorobimane | 380 | 461 |  |
| MPS (Methyl Green Pyronine Stilbene) | 364 | 395 |  |
| NBD | 466 | 539 |  |
| NBD Amine | 450 | 530 |  |
| Nile Red | 515-555, 559 | 590, 640 |  |
| Nitrobenzoxadidole | 465 | 510-650 |  |
| Noradrenaline | 340 | 490-520 |  |
| Nuclear Fast Red | 289-530 | 580 |  |
| Nuclear Yellow | 365 | 495 |  |
| Nylosan Brilliant Iavin E8G | 460 | 510 |  |
| Oregon Green | 503 | 522 |  |
| Oregon Green 488-X | 494 | 517 |  |
| Oregon Green ™ | 503 | 522 |  |
| Oregon Green ™ 488 | 490, 493 | 514, 520 |  |
| Oregon Green ™ 500 | 497 | 517 |  |
| Oregon Green ™ 514 | 506 | 526 |  |
| Pacific Blue | 405 | 455 |  |
| Pararosaniline (Feulgen) | 570 | 625 |  |
| PBFI | 340/380 | 420 | Excitation ratio dye |
| PE-Cy5 | 488 | 670 |  |
| PE-Cy7 | 488 | 755, 767 |  |
| PerCP | 488 | 675 |  |
| PerCP-Cy5.5 | 488 | 710 |  |
| PE-TexasRed [Red 613] | 488 | 613 |  |
| Phloxin B (Magdala Red) | 524 | 600 |  |
| Phorwite AR | 360 | 430 |  |
| Phorwite BKL | 370 | 430 |  |
| Phorwite Rev | 380 | 430 |  |
| Phorwite RPA | 375 | 430 |  |
| Phosphine 3R | 465 | 565 |  |
| PhotoResist | 365 | 610 |  |
| Phycoerythrin B [PE] | 546-565 | 575 |  |
| Phycoerythrin R [PE] | 565 | 578 |  |
| PKH26 (Sigma) | 551 | 567 |  |
| PKH67 | 496 | 520 | Chroma |
| PMIA | 341 | 376 |  |
| Pontochrome Blue Black | 535-553 | 605 |  |
| POPO-1 | 433 | 457 |  |
| POPO-3 | 533 | 574 |  |
| PO-PRO-1 | 435 | 455 |  |
| PO-PRO-3 | 539 | 567 |  |
| Primuline | 410 | 550 |  |
| Procion Yellow | 470 | 600 |  |
| Propidium Iodid (PI) | (305), 536, 538 | 617 |  |
| PyMPO | 412, 415 | 561, 564, 570 |  |
| Pyrene | 360 | 387 |  |
| Pyronine | 410 | 540 |  |
| Pyronine B | 540-590 | 560-650 |  |
| Pyrozal Brilliant Flavin 7GF | 365 | 495 |  |
| QSY 7 | 560 |  |  |
| Quinacrine Mustard | 440 | 510 |  |
| Red 613 [PE-TexasRed] | 488 | 613 |  |
| Resorufin | 571 | 584, 585 |  |
| RH 414 | 532 | 716 |  |

TABLE 1-continued

Fluorophores that may be used in the present method:

| Fluorophore | Absorption | Emission | Other info |
|---|---|---|---|
| Rhod-2 | 552 | 576 | |
| Rhodamine | 550 | 573 | |
| Rhodamine 110 | 496, 497 | 520 | |
| Rhodamine 123 | 507 | 529 | |
| Rhodamine 5 GLD | 470 | 565 | |
| Rhodamine 6G | 525 | 555 | |
| Rhodamine B | 540 | 625 | |
| Rhodamine B 200 | 523-557 | 595 | |
| Rhodamine B extra | 550 | 605 | |
| Rhodamine BB | 540 | 580 | |
| Rhodamine BG | 540 | 572 | |
| Rhodamine Green | 502 | 527 | |
| Rhodamine Phallicidine | 558, 542 | 575, 565 | |
| Rhodamine Phalloidine | 542 | 565 | |
| Rhodamine Red | 570 | 590 | |
| Rhodamine WT | 530 | 555 | |
| Rose Bengal | 525, 540 | 550-600 | |
| R-phycocyanine | | | |
| R-phycoerythrin (PE) | 565 | 578 | |
| rsGFP | 473 | 509 | red shifted GFP (S65T) |
| S65A | 471 | 504 | |
| S65C | 479 | 507 | |
| S65L | 484 | 510 | |
| S65T | 488 | 511 | |
| Sapphire GFP | 395 | 511 | |
| SBFI | 340/380 | 420 | Excitation ratio dye |
| Serotonin | 365 | 520-540 | |
| Sevron Brilliant Red 2B | 520 | 595 | |
| Sevron Brilliant Red 4G | 500 | 583 | |
| Sevron Brilliant Red B | 530 | 590 | |
| Sevron Orange | 440 | 530 | |
| Sevron Yellow L | 430 | 490 | |
| sgBFP ™ | 387 | 450 | |
| sgBFP ™ (super glow BFP) | 387 | 450 | Quantum's SuperGlo ™ GFP AFPs |
| sgGFP ™ | 474 | 488 | |
| sgGFP ™ (super glow GFP) | 474 | 509 | Quantum's SuperGlo ™ GFP AFPs |
| SITS | 336 | 436 | Ion Channels |
| SITS (Primuline) | 395-425 | 450 | |
| SITS (Stilbene Isothiosulphonic Acid) | 365 | 460 | |
| SNAFL calcein | 506/535 | 535/620 | Ratio Dye, pH |
| SNAFL-1 | 508/540 | 543/623 | Ratio Dye, pH |
| SNAFL-2 | 514/543 | 546/630 | Ratio Dye, pH |
| SNARF calcein | 552/574 | 590/629 | Ratio Dye, pH |
| SNARF1 | 576/548 | 635/587 | Excitation and emission ratio dye |
| Sodium Green | 506, 507 | 532 | Na+, K+ |
| SpectrumAqua | 433,/53 | 480/55 | Vysis |
| SpectrumGreen | 497/30, 509/31 | 538/44, 524/56 | Vysis |
| SpectrumOrange | 559/38, 560 | 588/48 | Vysis |
| Spectrum Red | 587, 587/35 | 612, 612/51 | |
| SPQ (6-methoxy-N-(3-sulfopropyl)quinolinium) | 344 | 443 | |
| Stilbene | 335 | 440 | |
| Sulphorhodamine B can C | 520 | 595 | |
| Sulphorhodamine G Extra | 470 | 570 | |
| SYTO 11 | 508, 510 | 527, 530 | Dye for DNA, RNA |
| SYTO 12 | 499, 500 | 522, 519 | Dye for DNA, RNA |
| SYTO 13 | 488, 491 | 509, 514 | Dye for DNA, RNA |
| SYTO 14 | 517, 521 | 549, 547 | Dye for DNA, RNA |
| SYTO 15 | 516, 518 | 546, 555 | Dye for DNA, RNA |
| SYTO 16 | 488, 494 | 518, 525 | Dye for DNA, RNA |

TABLE 1-continued

Fluorophores that may be used in the present method:

| Fluorophore | Absorption | Emission | Other info |
| --- | --- | --- | --- |
| SYTO 17 | 621 | 634 | Dye for DNA |
| SYTO 18 | 490, 493 | 507, 527 | Dye for DNA, RNA |
| SYTO 20 | 512 | 530 | Dye for DNA |
| SYTO 21 | 494 | 517 | Dye for DNA |
| SYTO 22 | 515 | 535 | Dye for DNA |
| SYTO 23 | 499 | 520 | Dye for DNA |
| SYTO 24 | 490 | 515 | Dye for DNA |
| SYTO 25 | 521 | 556 | Dye for DNA |
| SYTO 40 | 420 | 441 | Dye for DNA |
| SYTO 41 | 430 | 454 | Dye for DNA |
| SYTO 42 | 433 | 460 | Dye for DNA |
| SYTO 43 | 436 | 467 | Dye for DNA |
| SYTO 44 | 446 | 471 | Dye for DNA |
| SYTO 45 | 452 | 484 | Dye for DNA |
| SYTO 59 | 622 | 645 | Dye for DNA |
| SYTO 60 | 652 | 678 | Dye for DNA |
| SYTO 61 | 628 | 645 | Dye for DNA |
| SYTO 62 | 652 | 676 | Dye for DNA |
| SYTO 63 | 657 | 673 | Dye for DNA |
| SYTO 64 | 599 | 619 | Dye for DNA |
| SYTO 80 | 531 | 545 | Nucleic Acid Stain |
| SYTO 81 | 530 | 544 | Nucleic Acid Stain |
| SYTO 82 | 541 | 560 | Nucleic Acid Stain |
| SYTO 83 | 543 | 559 | Nucleic Acid Stain |
| SYTO 84 | 567 | 582 | Nucleic Acid Stain |
| SYTO 85 | 567 | 583 | Nucleic Acid Stain |
| SYTOX Blue | 445 | 470 | Nucleic Acid Stain |
| SYTOX Green | 504 | 523 | Nucleic Acid Stain |
| SYTOX Orange | 547 | 570 | Nucleic Acid Stain |
| Tetracycline | 390-425 | 525-560 | |
| Tetramethylrhodamine (TRITC) | 555 | 576 | |
| Texas Red ™ | 595 | 620 | |
| Texas Red-X ™ conjugate | 595 | 615 | |
| Thiadicarbocyanine (DiSC3) | 651, 653 | 674, 675 | |
| Thiazine Red R | 596 | 615 | |
| Thiazole Orange | 510 | 530 | |
| Thioflavin 5 | 430 | 550 | |
| Thioflavin S | 430 | 550 | |
| Thioflavin TCN | 350 | 460 | |
| Thiolyte | 370-385 | 477-488 | |
| Thiozole Orange | 453 | 480 | |
| Tinopol CBS (Calcofluor White) | 390 | 430 | |
| TMR | 550 | 573 | |
| TO-PRO-1 | 515 | 531 | |
| TO-PRO-3 | 644 | 657 | |
| TO-PRO-5 | 747 | 770 | |
| TOTO-1 | 514 | 531, 533 | |
| TOTO-3 | 642 | 660 | |
| TriColor (PE-Cy5) | (488) 650 | 667 | |
| TRITC TetramethylRodamineIsoThioCyanate | 550 | 573 | |
| True Blue | 365 | 425 | |
| TruRed | 490 | 695 | |
| Ultralite | 656 | 678 | |
| Uranine B | 420 | 520 | |
| Uvitex SFC | 365 | 435 | |
| wt GFP | 395 (475) | 508 | wild type GFP |
| WW | 781 | 605 | 639 |
| X-Rhodamine | 580 | 605 | |
| XRITC | 582 | 601 | |
| Xylene Orange | 546 | 580 | |
| Y66F | 360 | 508 | |
| Y66H | 360 | 442 | |
| Y66W | 436 | 485 | |

TABLE 1-continued

Fluorophores that may be used in the present method:

| Fluorophore | Absorption | Emission | Other info |
|---|---|---|---|
| Yellow GFP | 513 | 527 | Yellow shifted Green Fluorescent Protein |
| YFP | 513, 520 | 527, 532 | Yellow Fluorescent Protein |
| YO-PRO-1 | 491 | 506 | |
| YO-PRO-3 | 613 | 629 | |
| YOYO-1 | 491 | 508, 509 | |
| YOYO-3 | 612 | 631 | |

The fluorophores listed in Table 1, along with many others, are commercially available from worldwide suppliers, including Molecular Probes, a division of ThermoFisher Scientific, Eugene, Oreg., USA.

Methods of attaching fluorophores to proteins and polypeptides are exceedingly well known and will not be discuss in any detail. For a complete overview of the subject with an extensive list of relevant literature citations, see Modesti (2011) "Fluorescent labeling of proteins," *Methods Mol Biol.* 783:101-20. See also Michael Z. Lin, Lei Wang (12 Jun. 2008) "Selective Labeling of Proteins with Chemical Probes in Living Cells," *Physiology* 23(3), 131-141. See also Sauer, Hofkens, and Enderlein, "Handbook of Fluorescence Spectroscopy and Imaging: From Ensemble to Single Molecules 1st Edition," © 2011, Wiley-VCH (Weinheim, Germany), ISBN-13: 978-3527316694.

FIG. 1 is a schematic diagram of the HIV-1 genome. As noted above, HIV expresses auxiliary proteins that activate phases of gene expression. Tat activates efficient transcription of HIV-1 pre-mRNA. Rev activates nuclear export of partially and unspliced viral mRNA. HIV also encodes HIV encodes accessory proteins that degrade cellular proteins in order to increase infectivity. Vif induces the degradation of the APOBEC3G restriction factor. Vpu induces the degradation of BST2/Tetherin restriction factor. Nef induces the degradation of SERINC5 restriction factor. Vpu, Nef, and Env induce the degradation of the CD4 receptor protein.

Figure 2A:
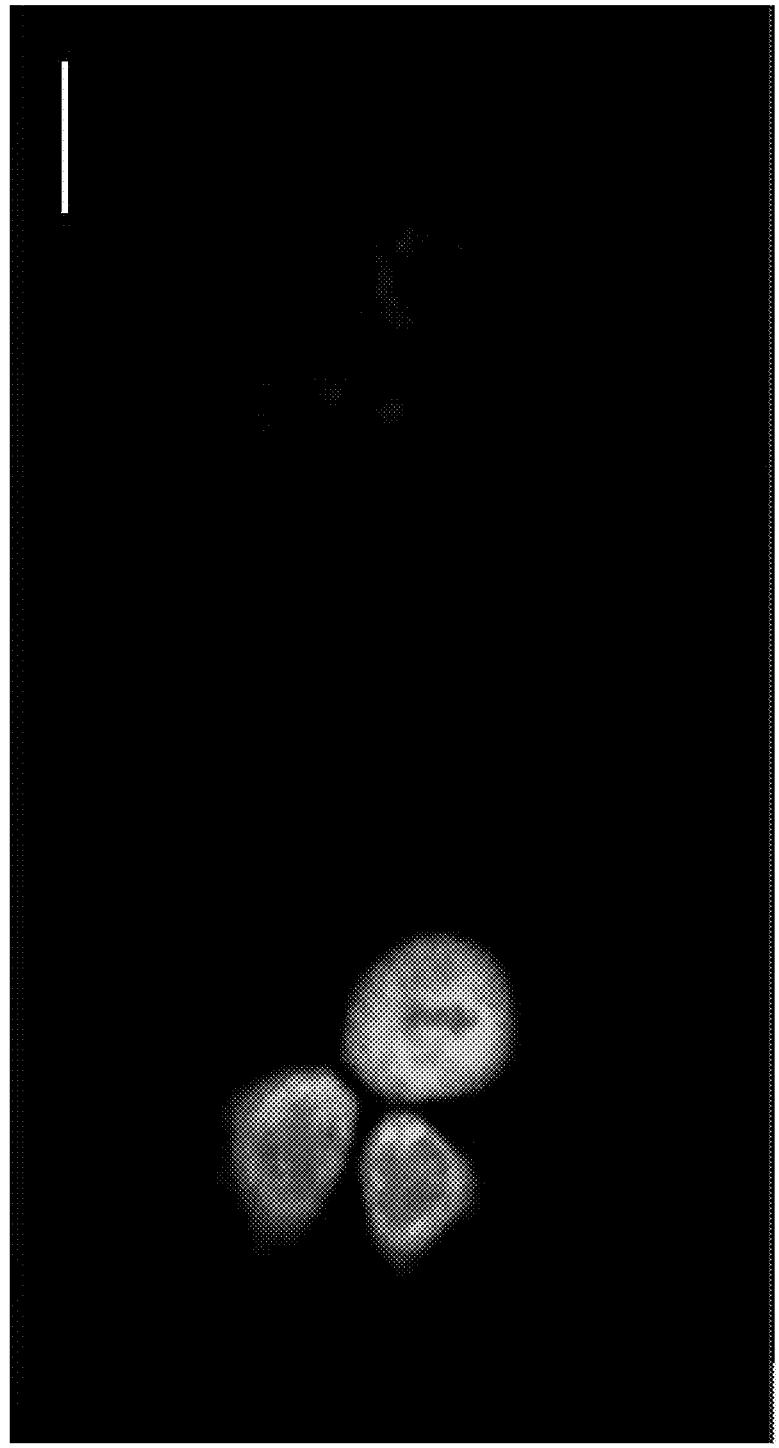
FIGS. 2A, 2B, 2C, 2D, and 2E are a series of time-lapse photomicrographs depicting ratiometric/multicolor HIV-1 reporter cells that combine reporter activation and reporter degradation to achieve a high signal-to-noise read-out of infection. As reporter 1 (blue) is activated by Tat/Rev, reporter 2 (green) is deactivated (degraded) by Vif, Elapsed time between FIG. 2A
Figure 2B:
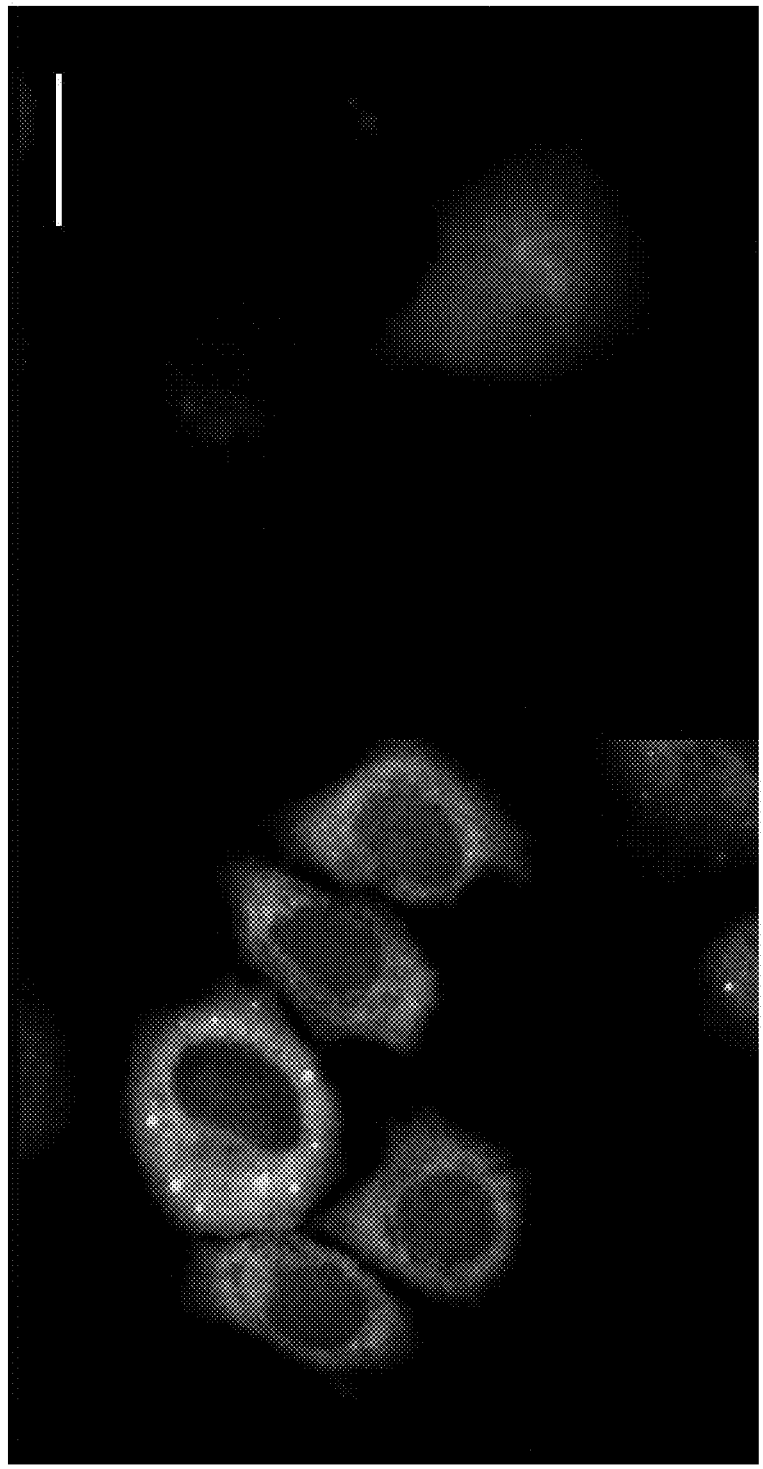
Figure 2C:
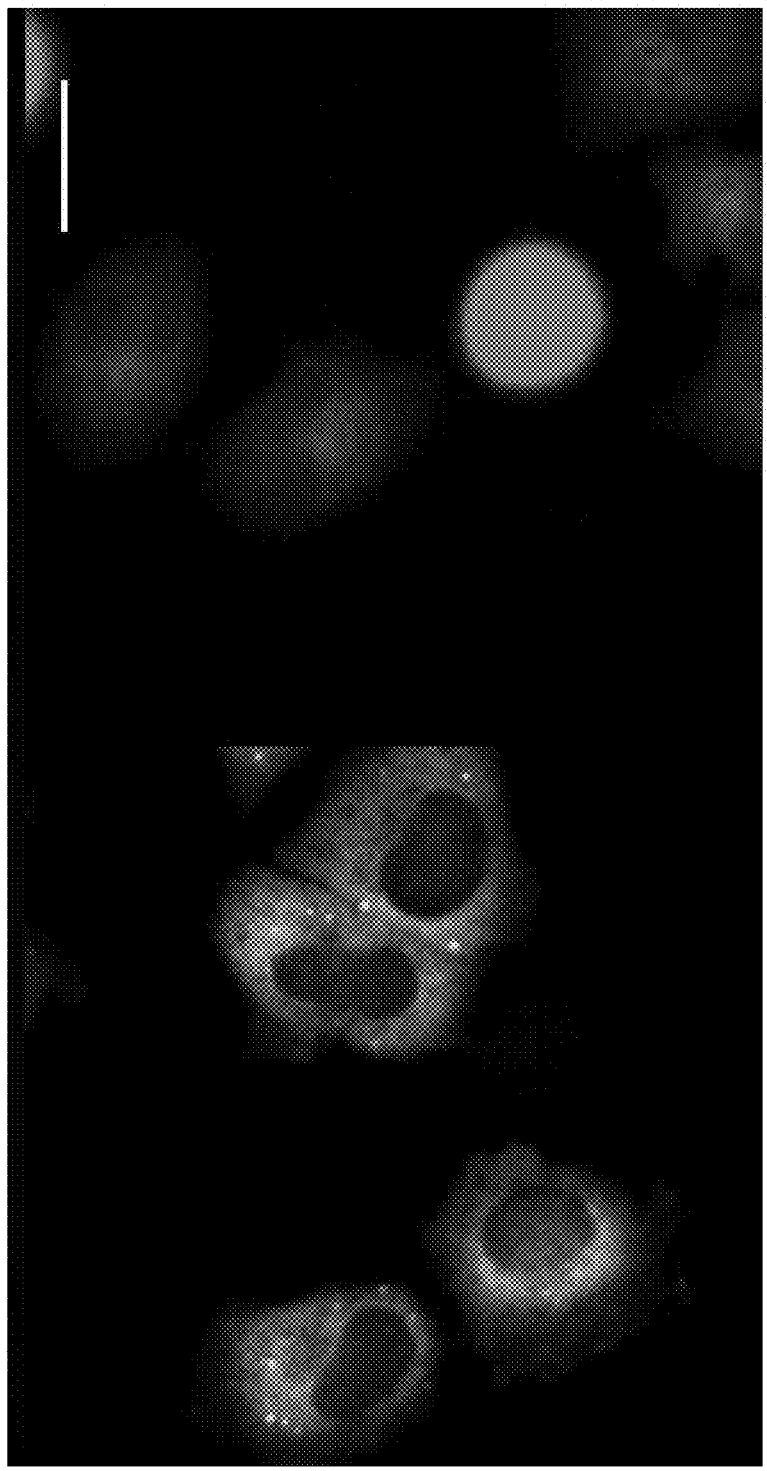
Figure 2D:
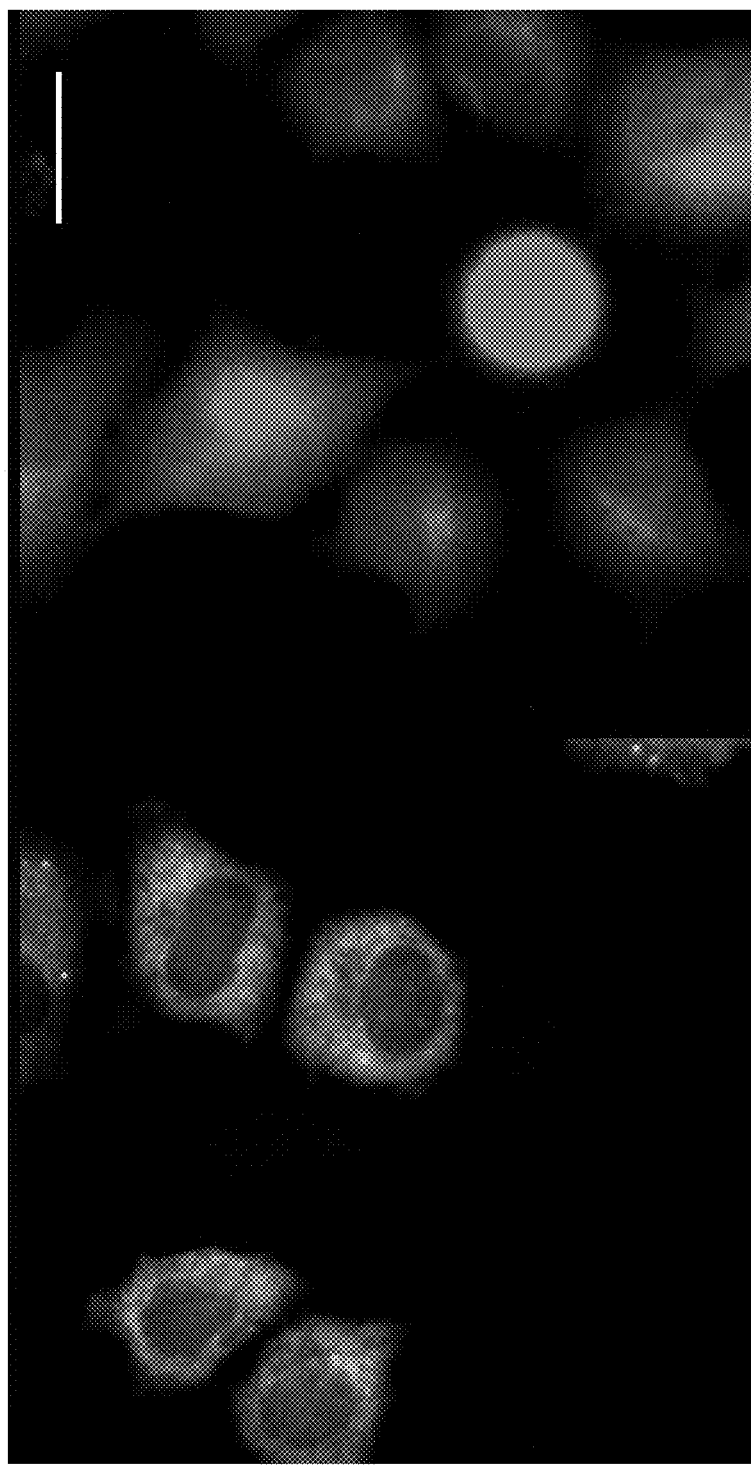
Figure 2E:
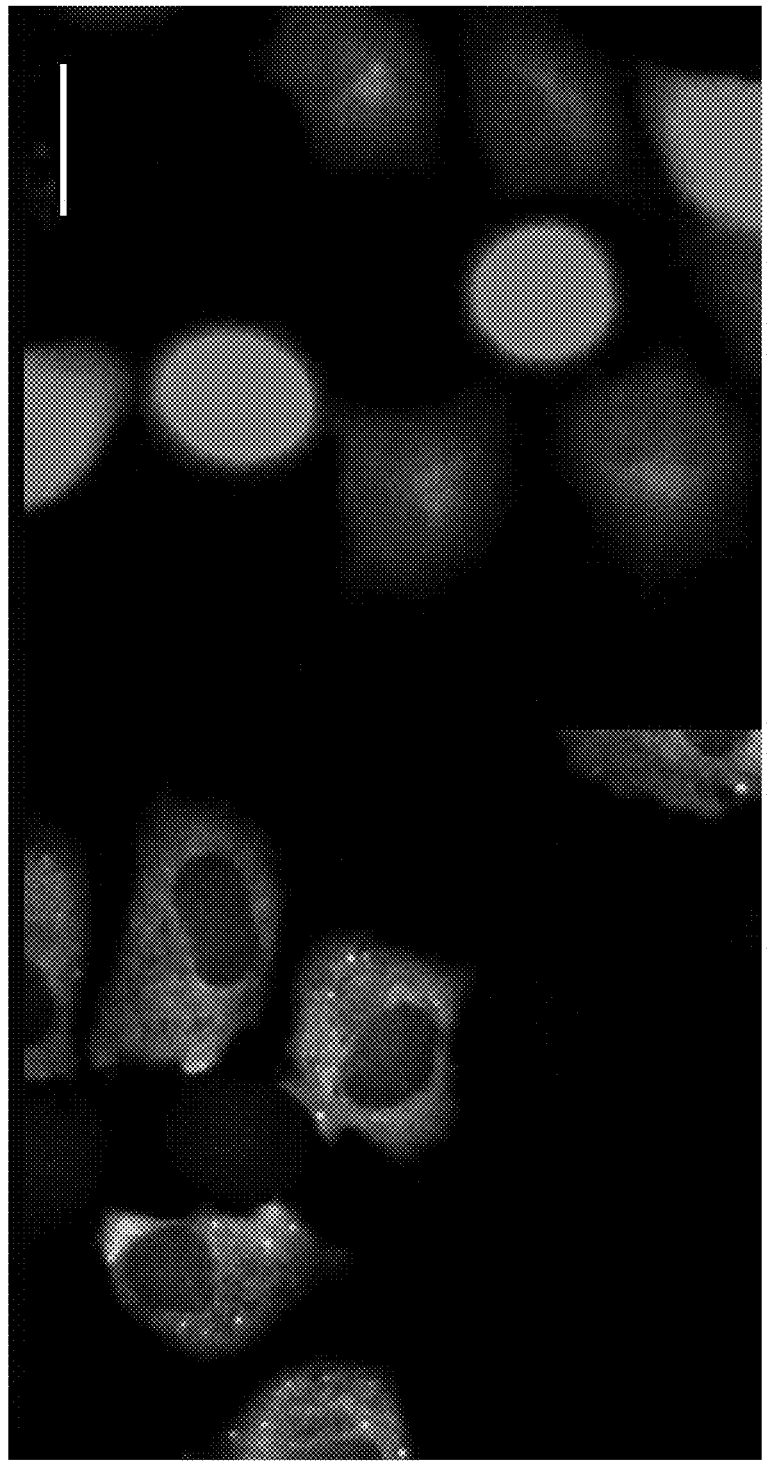

FIGS. 2A, 2B, 2C, 2D, and 2E are a series of time-lapse photomicrographs taken from a full motion picture depicting ratiometric/multicolor HIV-1 reporter cells that combine reporter activation and reporter degradation to achieve a high signal-to-noise read-out of infection. As reporter 1 (blue) is activated by Tat/Rev, reporter 2 (green) is deactivated (degraded) by Vif, Elapsed time between FIG. 2A and FIG. 2E is 12 hours. Images generated from VSVg pseudotyped HIV-1 cyan fluorescent protein (CFP) expressed from Nef position.

Figure 3B:
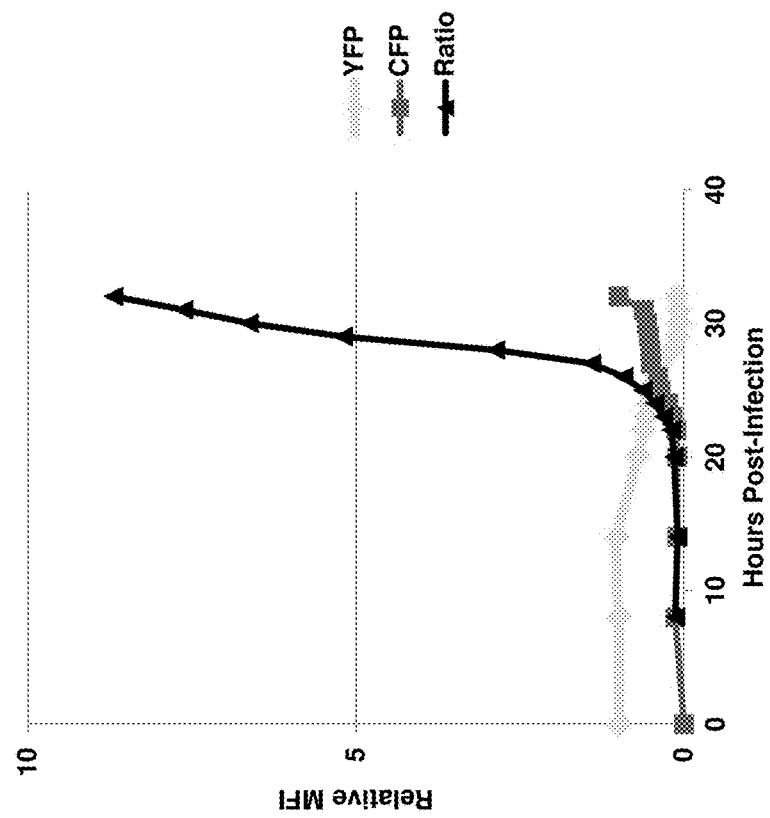
FIG. 3B is a corresponding graph that presents the same data as in FIG. 3A, with the addition of a trace showing the ratio between the signal from reporters 1 and 2 (black triangles).
Figure 3A:
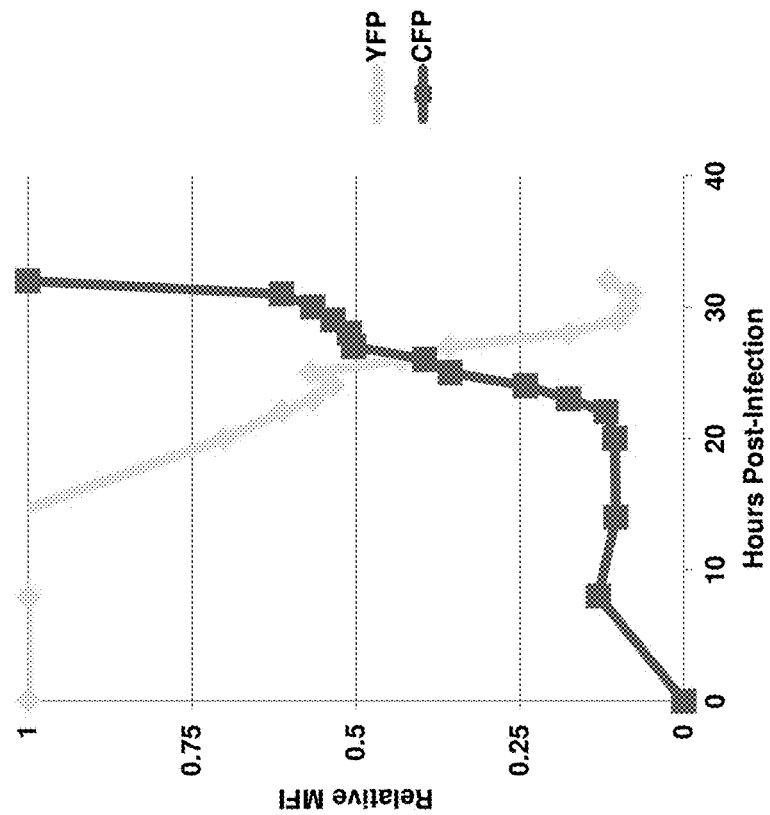
FIG. 3A is a graph showing the deactivation of reporter 2 superimposed upon the activation of reporter 1 over time. Yellow diamonds are reporter 2 (yellow fluorescent protein; YFP); blue squares are reporter 1 (cyan fluorescent protein; CFP). The graph thus depicts the rate of YFP-A3G (yellow) downregulation and HIV-1 (blue) upregulation over 35 hours of infection.

FIG. 3A is a graph depicting signal intensity from the test run shown in FIGS. 2A through 2E. Here, the deactivation of reporter 2 (the green cells in FIGS. 2A-2E) superimposed upon the activation of reporter 1 (the blue cells in FIGS. 2A-2E) over time. Yellow diamonds in FIG. 3A are fluorescent values for reporter 2 (yellow fluorescent protein; YFP); blue squares in FIG. 3A are fluorescent values for reporter 1 (cyan fluorescent protein; CFP). The graph thus depicts the rate of YFP-A3G (yellow) downregulation and HIV-1 (blue) upregulation over 35 hours of infection.

FIG. 3B is a corresponding graph that presents the same data as in FIG. 3A, with the addition of a trace showing the ratio between the signal from reporters 1 and 2 (black triangles). As shown in FIG. 3B, using the ratio of activation:degradation fluorescence provides ~10-fold increase to sensitivity of the assay. By using the ratio of the two signals, the time point at which HIV infection and replication begins to occur can also be precisely pinpointed.

Figure 4:
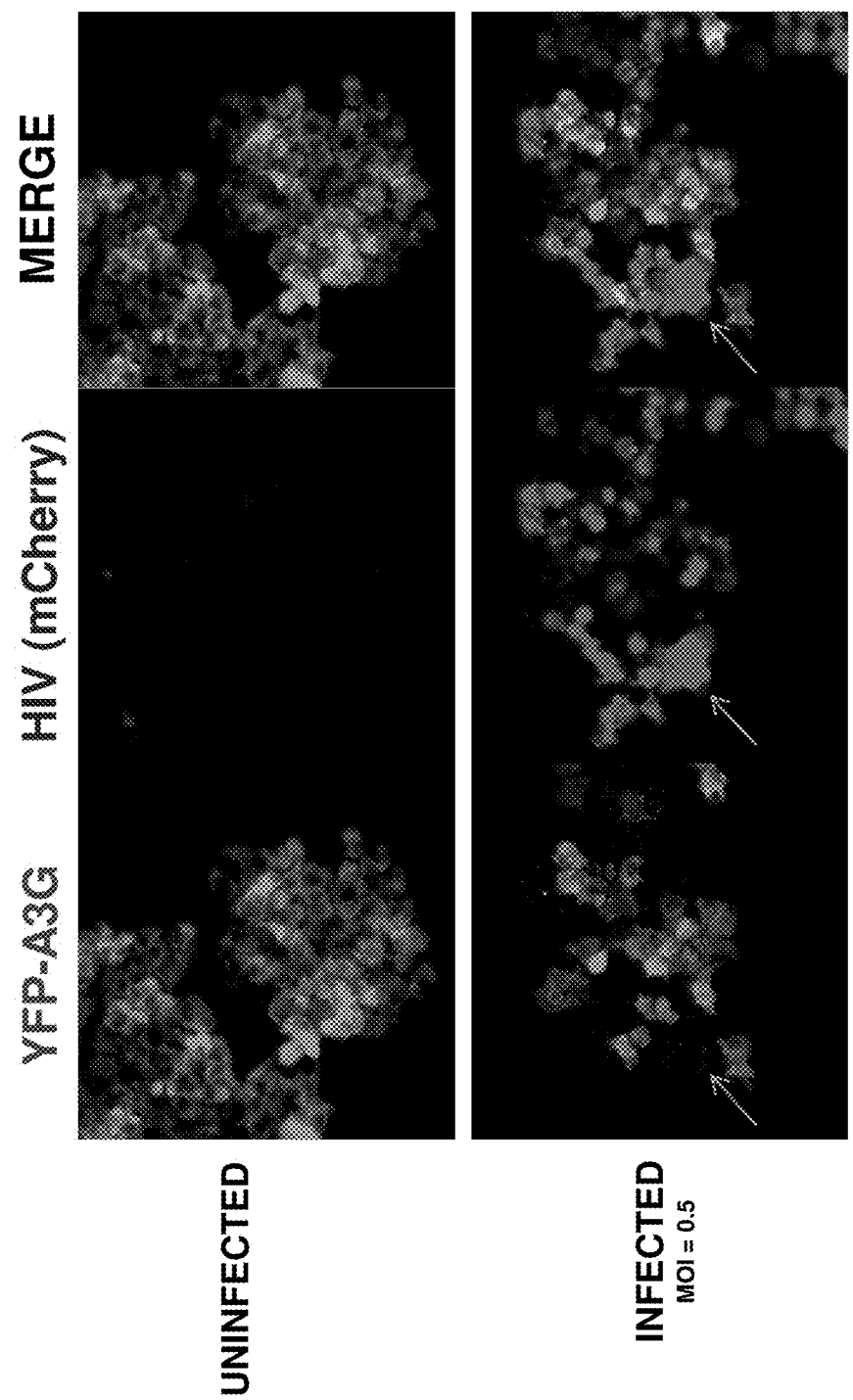
FIG. 4 is a pair of photomicrographs comparing the assay results in uninfected cells (top panel) and 24 hours after exposure to HIV in infected cells (bottom panel). As shown in the bottom panel of the figure, at 24 hours post-infection, the activation signal (reporter 1; red) is robust, while the degradation signal (reporter 2; green) is near background. The HIV-1-infected cells (which fluoresce brightly red) are clearly differentiated from the uninfected cells (which do not fluoresce red). In other words, when uninfected (top panel), cells are green due to YFP-APOBEC3G expression. Upon infection, the cells turn on a mCherry reporter (red) that responds to Rev and Tat, while the YFP-A3G (green) signal disappears due to Vif activity.

FIG. 4 is a pair of photomicrographs comparing the assay results in uninfected cells (top panel) and 24 hours after exposure to HIV in infected cells (bottom panel). As shown in the bottom panel of the figure, at 24 hours post-infection, the activation signal (reporter 1; red) is robust, while the degradation signal (reporter 2; green) is near background. The HIV-1-infected cells (which fluoresce brightly red) are clearly differentiated from the uninfected cells (which do not fluoresce red). In other words, when uninfected (top panel), cells are green due to YFP-APOBEC3G expression. Upon infection, the cells turn on a mCherry reporter (red) that responds to Rev and Tat, while the YFP-A3G (green) signal disappears due to Vif activity.

Figure 5:
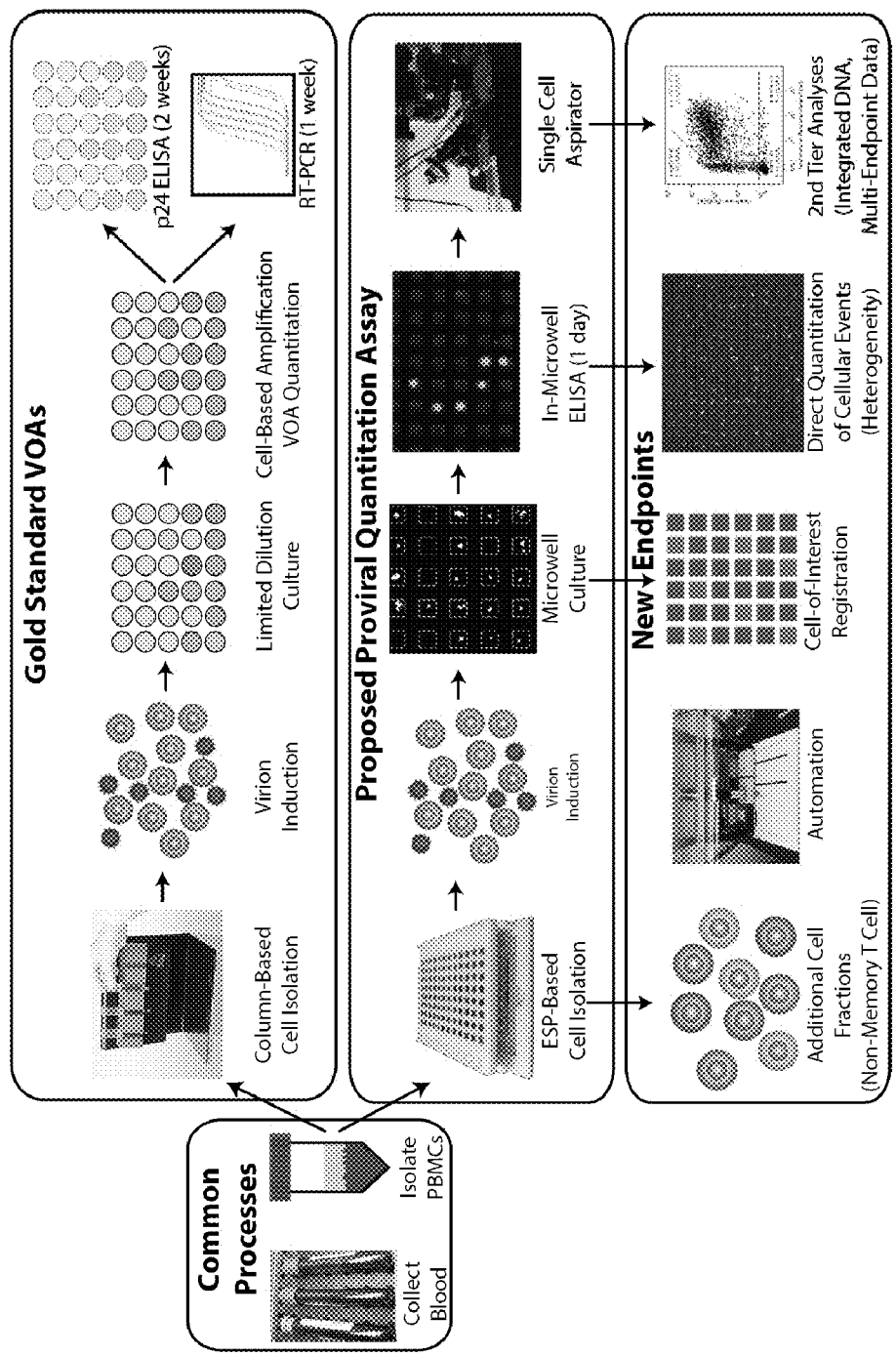
FIG. 5 is a schematic diagram contrasting conventional quantitative viral outgrowth assays (top panel) versus the method disclosed herein.

FIG. 5 is a schematic diagram contrast conventional quantitative viral outgrowth assays (top panel) versus the method disclosed herein. As shown in the bottom panel of FIG. 5, the method disclosed herein can be formatted as microfluidics-based quantitative virus outgrowth assay (Q-VOA) for detecting HIV-infected cells from infected people and measuring levels of productive infection.

Any cell subject to viral infection can be used in the assay. HeLa cells and Jurkat cells are preferred. HeLa cells are hardy, reliable, and readily form monolayers. This makes them excellent for image acquisition and analysis. Jurkat cells are likewise hardy and reliable. They are also exhibit migratory (seek and find) behaviors and may be superior for detecting virus in tissues.

Figure 6A:
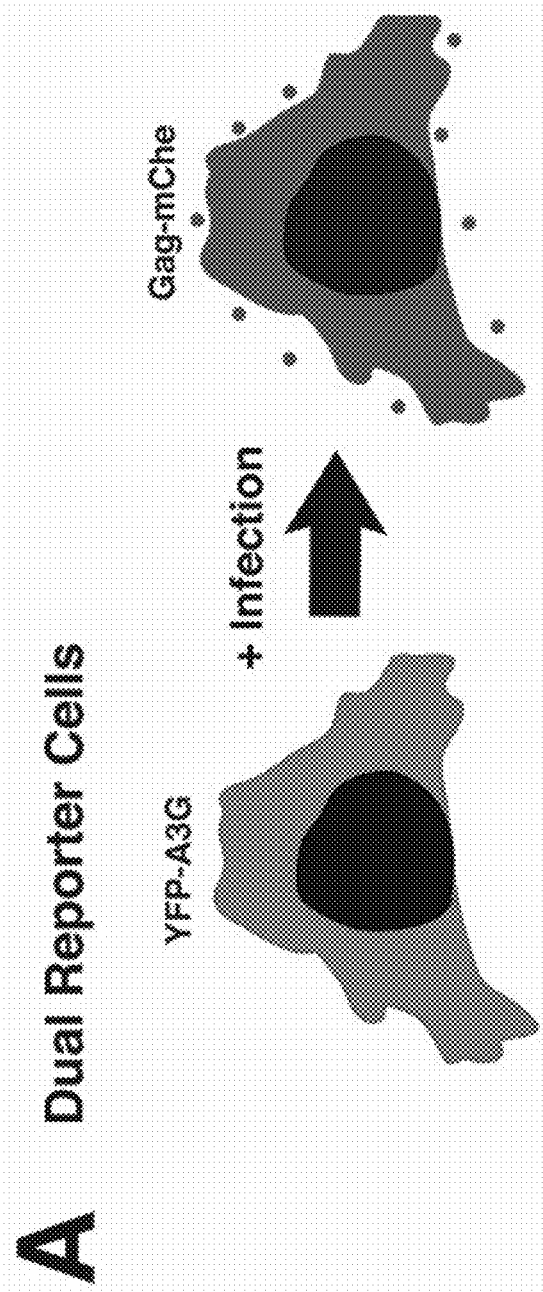
FIG. 6A is a schematic diagram of a HIV-susceptible HeLa or Jurkat cell constitutively expressing YFP-tagged APOBEC3G (YFP-A3G; green) and encoding an HIV-responsive reporter gene expressing HIV Gag fused to mCherry (Gag-mChe; red).

By way of a working example, the method has been implemented and shown to function as described. The basic functionality of the method is shown schematically in FIG. 6A. Here is depicted a schematic diagram of a HIV-susceptible HeLa or Jurkat cell constitutively expressing YFP-tagged APOBEC3G (YFP-A3G; green) and encoding an HIV-responsive reporter gene expressing HIV Gag fused to mCherry (Gag-mChe; red). Pre-infection, as shown in the left side of FIG. 6A, the cell yields no signal from the first fluorophore, which generates a first fluorescent signal—the red reporter Gag-mChe. This first fluorescent signal is upregulated only after productive infection of the cell. The second fluorophore (YFP-A3G; green), generates a robust signal in the left portion of FIG. 6A. This second fluorescent signal is down-regulated after productive infection of the cell. Thus, as shown in FIG. 6A, when the cell is infected, the first fluorescent signal (the red signal generated by Gag-mChe) is turned on; the second fluorescent signal (the green signal generated by YFP-A3G) is turned off.

Figure 6B:
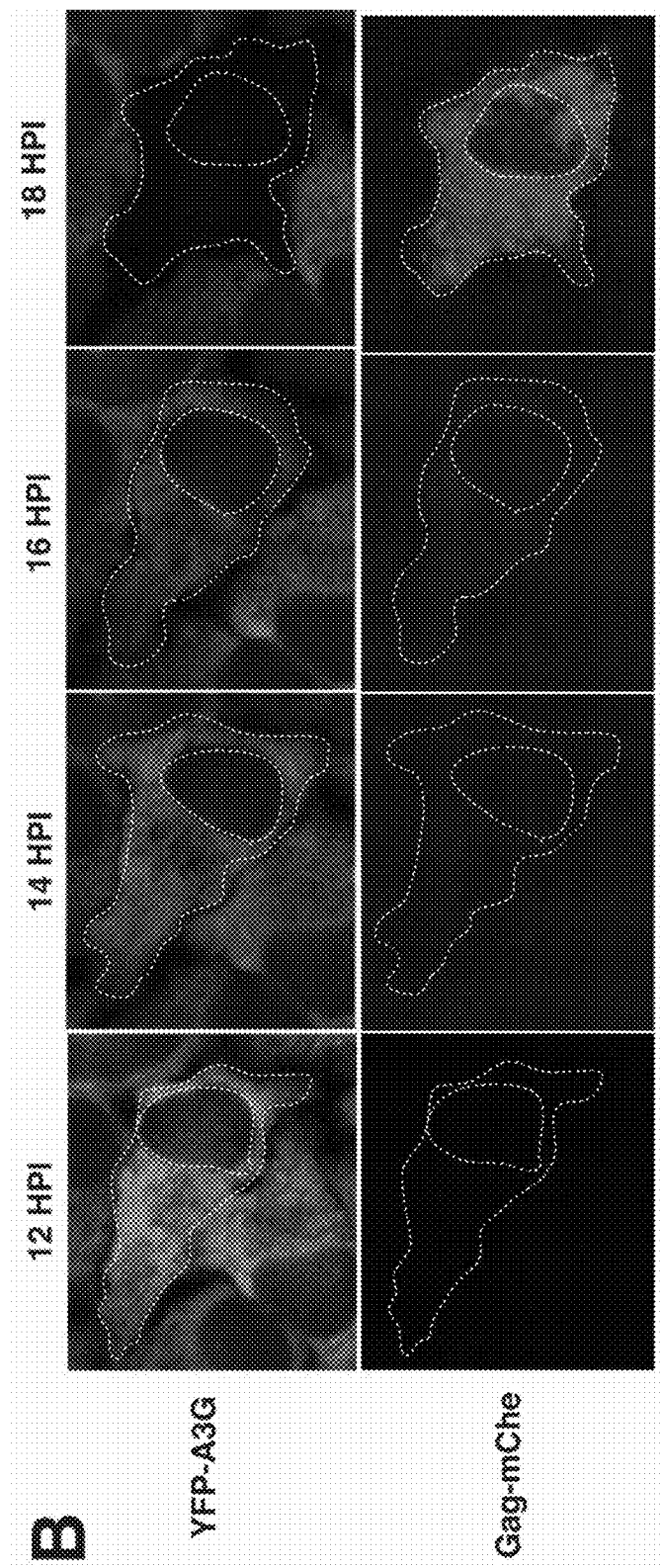
FIG. 6B is a series of photomicrographs depicting productive infection of HeLa cells. As shown in the top series of photos, infection leads to the downregulation of YFP-A3G (green) due to expression of the viral Vif protein that degraded YFP-A3G. Simultaneously, as shown in the bottom series of photos, infection leads to activation of Gag-mCherry (red) gene expression due to HIV Tat and Rev activity. "HPI" means "hours post-infection."

This is shown in real time in FIG. 6B, which shows the course of the up-regulation of the first fluorescent signal (red) and the simultaneous down-regulation of the second fluorescent signal (green) over the course of 18 hours post-infection (HPI) in a single HeLa cell. FIG. 6B is a series of photographs depicting productive infection of a HeLa cell with HIV in which the cells was modified to contain a first fluorophore and a second fluorophore as described herein. As shown in the top series of photos, infection led to the downregulation of YFP-A3G (green, the second fluorphore) due to expression of the viral Vif protein that degraded YFP-A3G. Simultaneously, as shown in the bottom series of photos, infection leads to activation of Gag-mCherry (red, the first fluorophore) gene expression due to the increased activities of HIV Tat and Rev.

Figures 6C, 6D:
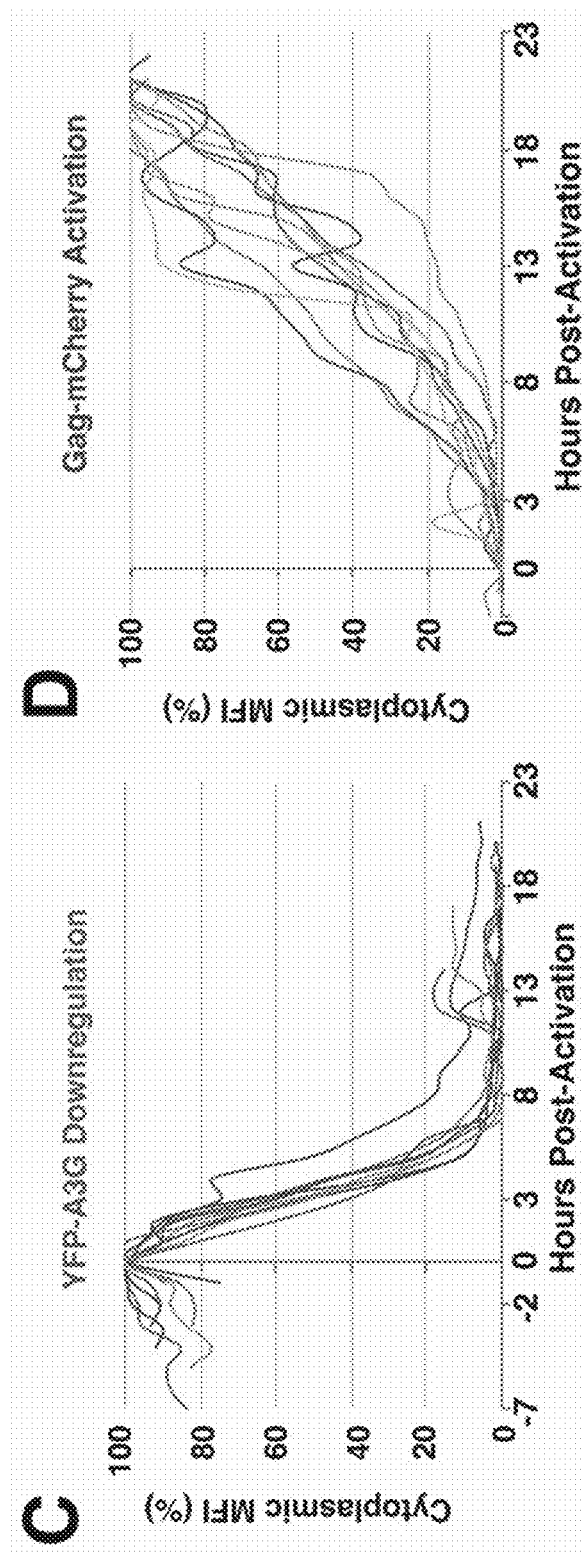
FIG. 6C is a graph depicting quantification of YFP-A3G downregulation kinetics for 10 cells based on measurements of cytoplasmic mean fluorescence intensity (MFI) over time.
FIG. 6D is a graph depicting quantification of viral activation kinetics for the same cells shown in FIG. 6C and tracking measurements of Gag-mChe expression.

FIGS. 6C and 6D are graphs showing the mean fluorescent intensity in ten (10) individual cells for YFP-A3G down-regulation kinetics (FIG. 6C) and up-regulation for Gag-mChe expression (FIG. 6D). These two graphs very neatly show the clean down-regulation of YFP-A3G as the infection progresses, and the simultaneous up-regulation of Gag-mChe over the same time period. At around 23 hours post-infection, the signals from YFP-A3G have bottomed out, while the signals from Gag-mChe have reached maxima.

Figure 7A:
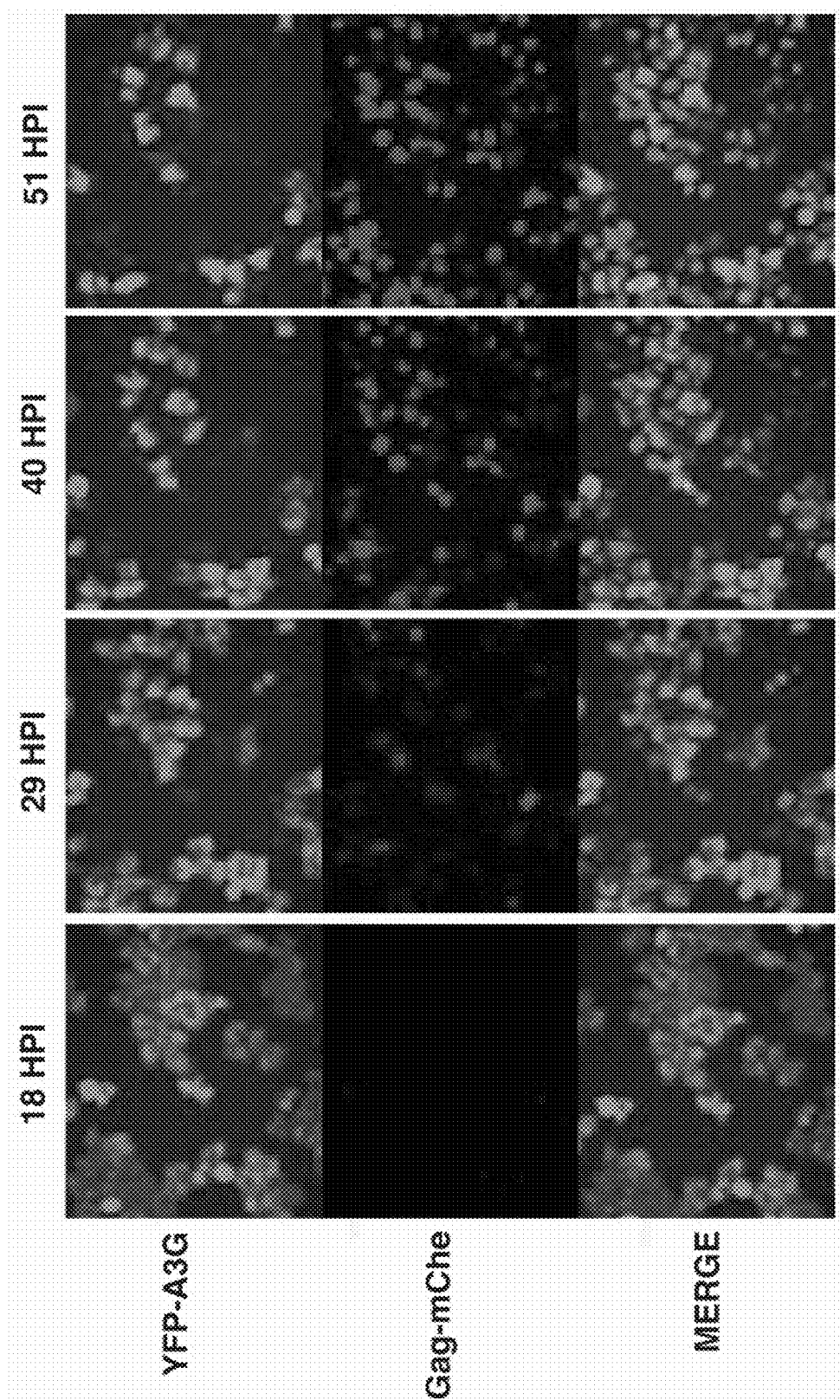
FIG. 7A is a series of photomicrographs showing whole-field read-outs using multicolor reporter cells. Shown here are HeLa reporter cells constitutively expressing YFP-tagged APOBEC3G (YFP-A3G; green) and encoding an HIV-responsive reporter gene expressing HIV Gag fused to mCherry (Gag-mChe; red) tracked over 51 hours post-infection ("HPI"). Approximately 50% of the cells were infected and turned from green to red.

The method is equally useful when analyzing large collections of cells, rather than single cells. FIG. 7A is a series of photomicrographs showing whole-field read-outs using the same multicolor reporter cells as used in FIG. 6B. Shown in FIG. 7A are HeLa reporter cells constitutively expressing YFP-tagged APOBEC3G (YFP-A3G; green) and encoding an HIV-responsive reporter gene expressing HIV Gag fused to mCherry (Gag-mChe; red) tracked over 51 hours post-infection ("HPI"). Approximately 50% of the cells were infected and turned from green to red. In the same fashion as described previously, the green signal was down-regulated upon infection, while the red signal was up-regulated upon infection.

FIG. 7B is a graph depicting whole-field mean fluorescence intensity (MFI) as a function of time (hours post-infection) for both the green signal and the red signal. A great many useful metrics can be gleaned from the graph shown in FIG. 7B. Plotting both signals on a single grid allow for the direct measurement of (1) cell doubling rate; (2) A3G downregulation kinetics; (3) viral gene activation; (4) rates of viral late gene expression; and (5) onset of virus particle production (based on changes to cell granularity).

FIG. 7C is a graph depicting the ratio of Gag signal to the A3G signal (Gag:A3G). This graph illustrates another useful feature of the cells, namely the signal-to-noise can be reduced by calculating the ratio of the relative measurements of YFP-A3G and Gag-mCherry signals. By using this ratio, the signal is unmistakable from any noise.

What is claimed is:

1. A method of tracking viral infection of a cell, the method comprising:
   (a) providing a cell susceptible to infection by a virus in which the cell comprises:
      a first nucleic acid encoding a gene that constitutively expresses a first fusion protein, wherein the first fusion protein comprises (i) a first domain susceptible to degradation by a protein from the virus, and (ii) a second domain comprising a first protein fluorophore; and
      a second nucleic acid encoding a second fusion protein, wherein the second fusion protein comprises (i) a first domain operably linked to a promoter that is responsive to infection by the virus, and (ii) a second domain comprising a second protein fluorophore;
      wherein a fluorescent signal from the first protein fluorophore is down-regulated upon infection of the cell by the virus, and a fluorescent signal from the second protein fluorophore is up-regulated upon infection of the cell by the virus;
   (b) exposing the cell to the virus under conditions where the virus can infect the cell;
   (c) measuring the fluorescent signals generated by the first protein fluorophore and the second protein fluorophore; and
   (d) determining the extent of infection of the cell by the virus by comparing the fluorescent signals measured in step (c) with corresponding signals generated in a corresponding cell not exposed to the virus.

2. The method of claim 1, wherein the cell is a human T-cell.

3. The method of claim 1, wherein the cell is a HeLa cell or a Jurkat cell.

4. The method of claim 1, wherein the virus is an HIV virus.

5. The method of claim 4, wherein the cell is a human T-cell.

6. The method of claim 4, wherein the cell is a HeLa cell or a Jurkat cell.

7. The method of claim 1, wherein the virus is an HIV-1 virus.

8. The method of claim 7, wherein the cell is a human T-cell.

9. The method of claim 7, wherein the cell is a HeLa cell or a Jurkat cell.

10. The method of claim 1, wherein the second fusion protein comprises Tat (trans-activator of transcription) or Rev.

11. The method of claim 1, wherein the first fusion protein comprises a protein selected from the group consisting of A3G (apolipoprotein B mRNA editing enzyme), BST2 (bone marrow stromal antigen 2, CD4 (cluster of differentiation 4), and SERINC5 (serine incorporator 5).

12. The method of claim 1, wherein:
   The second fusion protein comprises Tat (trans-activator of transcription) or Rev; and
   the first fusion protein comprises a protein selected from the group consisting of A3G, BST2, CD4, and SERINC5.

13. The method of claim 12, wherein the cell is a human T-cell, a HeLa cell, or a Jurkat cell.

14. The method of claim 13, wherein the virus is an HIV virus.

15. The method of claim 13, wherein the virus is an HIV-1 virus.

16. The method of claim 1, wherein in step (a) the cell contains a third nucleic acid encoding a gene that constitutively expresses a third fusion protein, wherein the third fusion protein comprises (i) a first domain susceptible to alteration by a protein from the virus, and (ii) a second domain comprising a third protein fluorophore; and wherein the third protein fluorophore generates a fluorescent signal that is distinct from and can be detected independently of the fluorescent signals generated by the first and second protein fluorophores, and wherein the fluorescent signal generated from the third protein fluorophore is detectably altered upon infection of the cell with the virus.

17. The method of claim 16, wherein in step (a) the cell contains a fourth nucleic acid encoding a gene that constitutively expresses a fourth fusion protein, wherein the fourth fusion protein comprises (i) a first domain susceptible to alteration by a protein from the virus, and (ii) a second domain comprising a fourth protein fluorophore; and wherein the fourth protein fluorophore generates a fluorescent signal that is distinct from and can be detected independently of the signals generated by the first, second, and third protein fluorophores, and wherein the fluorescent signal generated from the fourth protein fluorophore is detectably altered upon infection of the cell with the virus.

18. The method of claim 17, wherein in step (a) the cell contains a fifth nucleic acid encoding a gene that constitutively expresses a fifth fusion protein, wherein the fifth fusion protein comprises (i) a first domain susceptible to alteration by a protein from the virus, and (ii) a second domain comprising a fifth protein fluorophore; and wherein the fifth protein fluorophore generates a fluorescent signal that is distinct from and can be detected independently of the signals generated by the first, second, third, and fourth protein fluorophores, and wherein the fluorescent signal generated from the fifth protein fluorophore is detectably altered upon infection of the cell with the virus.

\* \* \* \* \*